(12) United States Patent
Van den Heuvel et al.

(10) Patent No.: US 7,779,153 B2
(45) Date of Patent: Aug. 17, 2010

(54) AUTOMATED COLLECTION OF OPERATIONAL DATA FROM DISTRIBUTED MEDICAL DEVICES

(75) Inventors: Koen Van den Heuvel, Hove (BE); Sven Haemers, Brussels (BE); Sfen Mertens, Aartselaar (BE); Philip Smet, Beervelde (BE); Geert Smits, Berchem (BE)

(73) Assignee: Cochlear Limited, Lane Cove, New South Wales (AU)

( * ) Notice: Subject to any disclaimer, the term of this patent is extended or adjusted under 35 U.S.C. 154(b) by 840 days.

(21) Appl. No.: 11/588,265

(22) Filed: Oct. 27, 2006

(65) Prior Publication Data

US 2007/0198067 A1 Aug. 23, 2007

Related U.S. Application Data

(60) Provisional application No. 60/730,364, filed on Oct. 27, 2005.

(51) Int. Cl.
G06F 15/173 (2006.01)
H04R 29/00 (2006.01)
H04R 25/00 (2006.01)

(52) U.S. Cl. .................. 709/238; 709/223; 381/60; 381/315

(58) Field of Classification Search .......... 709/223, 709/224, 238; 381/60, 312, 315; 607/136, 607/137
See application file for complete search history.

(56) References Cited

U.S. PATENT DOCUMENTS 4,617,913 A 10/1986 Eddington
5,095,904 A 3/1992 Seligman et al.
5,215,085 A 6/1993 Von Wallenberg-Pachaly
5,271,397 A 12/1993 Seligman et al.
5,683,432 A * 11/1997 Goedeke et al. ............ 607/32
5,722,999 A * 3/1998 Snell ......................... 607/32
5,724,433 A 3/1998 Enoebretson et al.
6,002,966 A 12/1999 Loeb et al.
6,219,580 B1 4/2001 Faltys et al.
6,728,578 B1 4/2004 Voelkel
7,221,646 B2 * 5/2007 Kawano et al. ............ 370/218
7,286,673 B2 * 10/2007 Bindner et al. ............. 381/60
2002/0054689 A1 * 5/2002 Zhang et al. ............... 381/312

FOREIGN PATENT DOCUMENTS

| AU | 1706592 | 1/1993 |
|---|---|---|
| EP | 0282335 B1 | 9/1988 |
| EP | 0282336 | 9/1988 |
| WO | 91/03913 | 3/1991 |

* cited by examiner

Primary Examiner—Larry Donaghue
Assistant Examiner—Brian J Gillis
(74) Attorney, Agent, or Firm—Connolly Bove Lodge & Hutz LLP

(57) ABSTRACT

A system and method for automatically collecting at a data repository operational data from remotely distributed medical apparatus via a network, is disclosed, the method comprising: automatically capturing operational data at said medical apparatus; automatically selecting a route through the network for transferring said captured operational data to said data repository; and automatically transmitting said captured operational data to said central medical location via said selected network route.

51 Claims, 17 Drawing Sheets

FIG. 8B

| MEDICAL APPARATUS IDENTIFIER | INTERNET ACCESSIBILITY | FRIEND ACCESSIBILITY | FRIEND-INTERNET ACCESS | REMARKS |
|---|---|---|---|---|
| 455413 | 50.23 | 0.01 | 0.5 | SCHOOL PC |
| 664123 | 100 | 0.0015 | 0.15 | HOSPITAL PC |
| 125112 | 1.24 | 0.1 | 0.13 | BTE FRIEND 1 |
| 654261 | 0.085 | 0.9 | 0.077 | BTE FRIEND 2 |

891 893 895 897 899

FRIENDS LIST 994

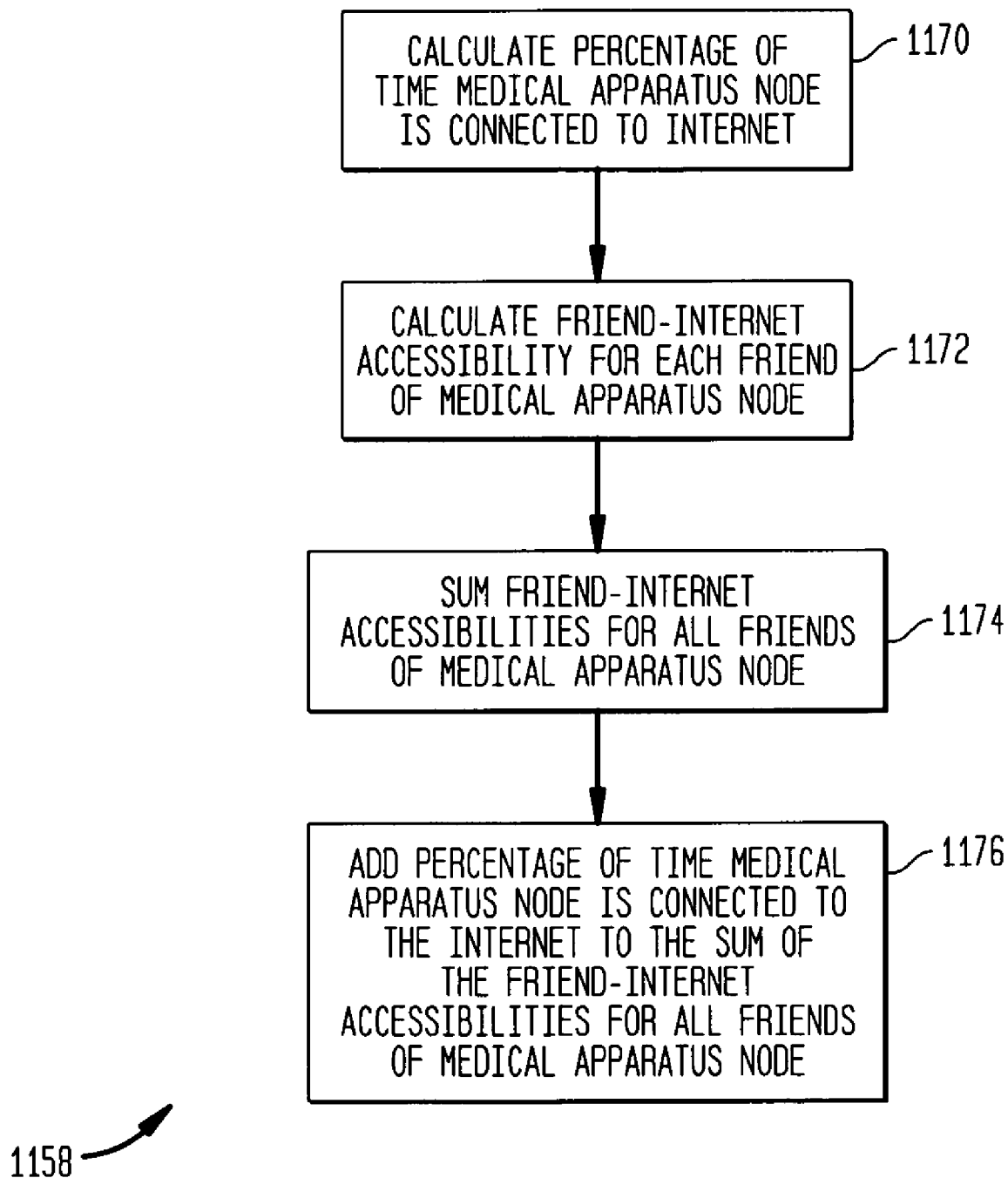

AUTOMATED COLLECTION OF OPERATIONAL DATA FROM DISTRIBUTED MEDICAL DEVICES

CROSS-REFERENCE TO RELATED APPLICATIONS

This application makes reference to and claims priority from U.S. Provisional Patent Application No. 60/730,364 filed Oct. 27, 2005, which is hereby incorporated by reference herein.

BACKGROUND

1. Field of the Invention

The present invention relates generally to medical devices, and more particularly, to the automated collection of operational data from distributed medical devices.

2. Related Art

The rate of advancement in technologies such as electronic packaging and assembly, semiconductors, microprocessors, and related technologies is accelerating. In the medical device industry such advancements are often motivated by a desire to miniaturize components to improve the mobility and/or portability of medical devices while simultaneously providing improved performance and increased functionality.

There are far-reaching consequences to improving the mobility or portability of medical devices, ranging from greater patient independence and quality of life to measurable cost savings. For example, a ventilator, defibrillator, ventricular assist device, infusion pump, blood pressure monitor, pacemaker, blood insulin monitor, and other medical devices may now follow a patient from the emergency room to the surgical facility to a recovery room and to their residence without interruption of therapy. Demographic, economic and other indicators suggest that this trend will continue to enable medical devices to travel with the patient outside of a medical facility thereby enabling the devices to perform their test, treatment, monitoring or other therapeutic functions.

More recently, there has been a desire or need to retrieve data from distributed medical devices to monitor the condition of the patient as well as the operational status and performance of the device, as well as to determine whether the device requires maintenance or modification. However it has traditionally been a challenge to collect such operational data.

Take, for example, prosthetic hearing devices such as hearing aids, middle ear implants, Cochlear™ implants, and the like. A hallmark of such devices since their inception has been their ability to provide increased functionality in a small package that is implanted and/or carrier on the body of the patient (commonly referred to as a "recipient"). Obtaining patient data stored in such devices, as well as to obtain information regarding the performance of the device has traditionally required the recipient to visit a medical facility to provide an audiologist or other health-care professional access to the device.

More recently, and for certain manufacturers seeking information regarding the medical devices they produce, patients and/or health-care professionals have been able to transmit certain information to the device manufacturer via mail, facsimile or, more recently, the Internet. Also, operational data associated with the use of prosthetic hearing devices and other medical devices is often fragmented, inaccurate, subjective, incomplete and/or not timely obtained.

Although there are many benefits associated with the more current approach of using the Internet, for example, by providing a website for entering user data, such an approach is not without its drawbacks. For example, this approach is not ideal for less confident users, and it is subject to the user to remember to enter the user data, as well as the ability if individual users to accurately enter the data. As a result, only a small segment of the user community will provide accurate and timely feedback. In addition, conventional web sites capture user data regardless of format or content, increasing the likelihood that such user data will be misinterpreted or inaccurate. Furthermore, conventional feedback mechanisms are often not objective representations of user data. As a result, operational data is often not made available to the appropriate person at the appropriate time.

SUMMARY

In one aspect of the present invention, a method for automatically collecting at a data repository operational data from remotely distributed medical apparatus via a network, is disclosed, the method comprising: automatically capturing operational data at said medical apparatus; automatically selecting a route through the network for transferring said captured operational data to said data repository; and automatically transmitting said captured operational data to said central medical location via said selected network route.

In another aspect of the present invention, a system for automatically collecting operational data from remotely distributed medical apparatus via a network is disclosed, the system comprising: a data repository; remotely distributed medical apparatus each configured to automatically capture operational data from the apparatus, to automatically select a route through the network for transferring said captured operational data from said medical apparatus to said data repository; and to automatically transmit said captured operational data to said data repository via said selected network route.

BRIEF DESCRIPTION OF THE DRAWINGS

Embodiments of the present invention will be described in conjunction with the accompanying drawings, in which:

FIG. 8B is an exemplary view of one embodiment of the friend list of FIG. 8A;

FIG. 11C is a detailed flowchart illustrating one embodiment of the process of calculating internet accessibility of a medical apparatus node of FIGS. 11A and 11B;

DETAILED DESCRIPTION

Figure 1A:
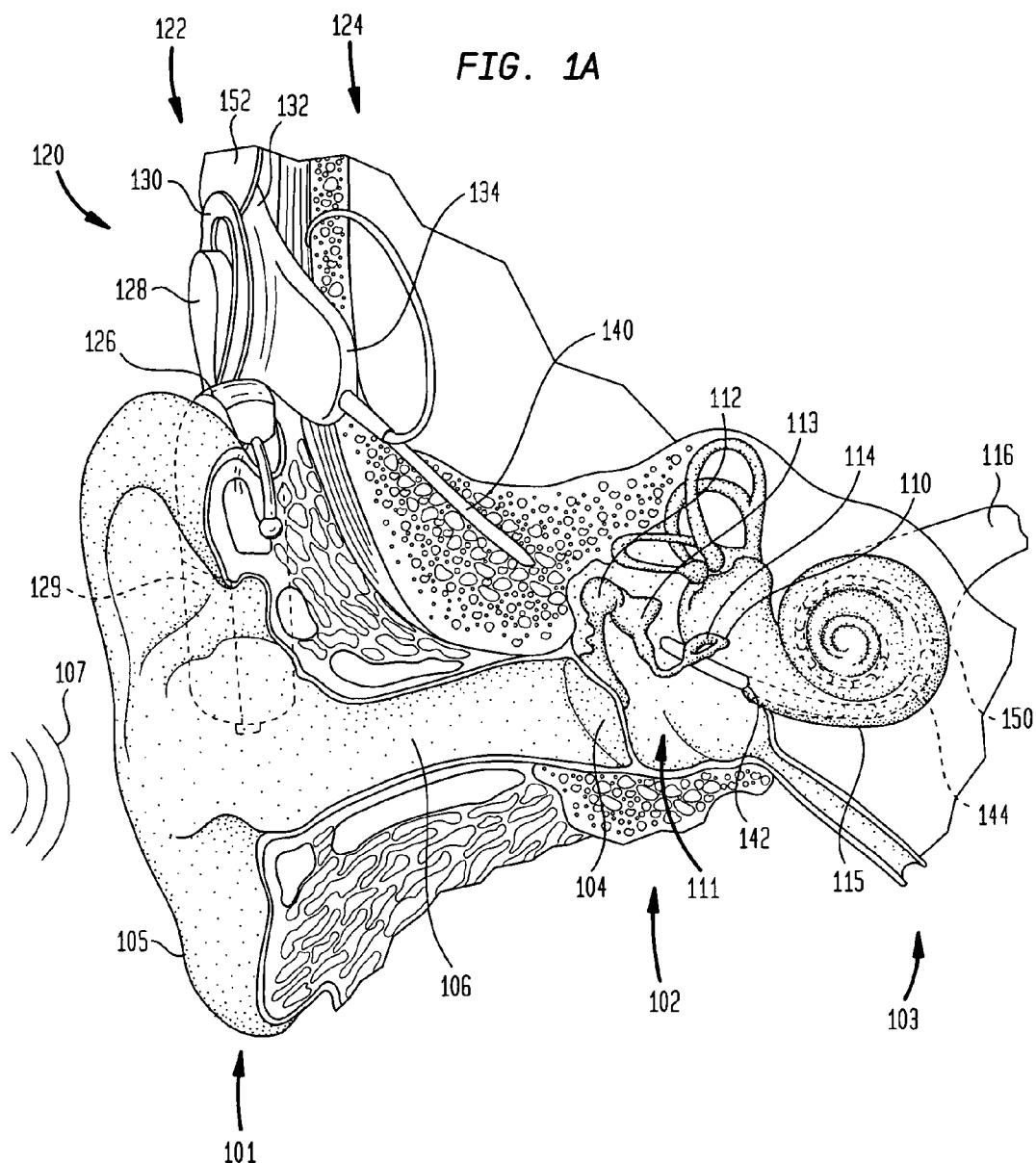
FIG. 1A is a perspective view of an exemplary hearing implant system suitable for implementing embodiments of the present invention.

Aspects of the present invention are generally directed to the automatic collection of performance, exception, patient and other data ("operational data" herein) from remotely distributed medical apparatus. Such medical apparatus may include portable medical devices as well as associated medical equipment for implanting, maintaining, programming or otherwise servicing medical devices. This automated collection of operational data from remotely distributed medical apparatus facilitates the storage of the operational data at a central data repository or elsewhere for subsequent or real-time analysis without reliance on the patient or health-care professional.

Specifically, embodiments of the present invention route the operational data from remotely distributed medical apparatus to a data repository (sometimes referred to as a medical device operational data repository) over a network. The network may be a computer network such as the Internet, local area network, wide-area network, and other computer network, a telephone network, any other network regardless of transmission medium thereof. A data acquisition and transfer module that is included in or operationally coupled to the portable medical apparatus facilitates the capture and routing of the operational data. The data acquisition and transfer module comprises a data capture module that collects and, if necessary, formats operational data received from the medical device. A data routing module of the data acquisition and transfer module transmits the captured operational data to the data repository. Medical apparatus that comprise or are operationally connected to a data transfer and acquisition module are at times referred to herein as a "medical apparatus node."

The network may provide a direct network connection from the data acquisition and transfer module to the operational data repository. The network may alternatively or additionally provide an indirect network connection between the data acquisition and transfer module and the data repository; that is, a route through one or more intermediate nodes. Thus, the data routing module may transmit the captured operational data to the data repository node directly or indirectly via one or more intermediate nodes. In addition to the medical apparatus nodes, the intermediate nodes preferably also include or are operationally coupled to a data routing module. In such embodiments both the medical apparatus nodes as well as the intermediate nodes determine a route from that node to one or more other intermediate nodes to facilitate the collocation of the operational data at the data repository node. In certain to determine a route over the network to the central medical location. The route selected by the data routing module at any given node may be based on one or more selection criteria including but no limited to, speed, safety of data, reliability, efficiency, etc.

Exemplary embodiments of the present invention are described herein in the context of a particular application, prosthetic hearing devices. The term "prosthetic hearing device" refers to any medical device that is able to assist a recipient's ability to hear sounds, improve that recipient's ability to hear sounds, or provide medical or therapeutic treatment to the auditory system. Typically such implants are used with recipients who experience some form of sensorineural hearing loss. Such devices include, but are not limited to, hearing aids, acoustic/mechanical stimulators, electrical stimulators, or hybrids thereof, such as electric-acoustic stimulators. Examples of acoustic/mechanical stimulators include middle-ear implants, vibrating implants, or bone-anchored hearing aids. The operation of an electrical stimulator is well understood in the art, and is described, for example, in U.S. Pat. No. 4,532,930, the entire contents and disclosures of which are hereby incorporated by reference herein. Examples of electrical prosthetic hearing implants include the Nucleus™ implant and Freedom™ implant manufactured by Cochlear Limited. The prosthetic hearing implant may comprise components which are completely implanted or may comprise a mix of components which are external, partially implanted or totally implanted. The prosthetic hearing implant may stimulate one or both ears, depending on the requirements of the recipient.

Hearing loss, which may be due to many different causes, is generally of two types, conductive and sensorineural. Conductive hearing loss occurs when the normal mechanical pathways which provide sound to hair cells in the cochlea are impeded, for example, by damage to the ossicles. Conductive hearing loss is often addressed with conventional prosthetic hearing devices, namely, hearing aids, which amplify sound so that acoustic information may reach the cochlea.

Profound deafness, however, is caused by sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to, or absence of, the mechanism that naturally generates nerve impulses from sound. As a result, prosthetic hearing implants such as Cochlear™ prostheses (commonly referred to as Cochlear™ prosthetic devices, Cochlear™ implants, Cochlear™ devices, and the like; simply "cochlear implants" herein) have been developed to provide persons with sensorineural hearing loss with the ability to perceive sound.

Prosthetic hearing devices are implanted by a surgeon, configured or customized by an audiologist, and maintained by a clinician. As noted, the patient or wearer of a prosthetic hearing device is referred to herein as a recipient and the surgeon, audiologist, clinician, etc., are referred to as healthcare professionals. Also, consistent with the above usage, the term "user" as used herein refers to any such recipient of a prosthetic hearing device or health-care professional.

FIG. 1 is a perspective view of an exemplary cochlear implant 120 in which embodiments of the present invention may be advantageously implemented. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In deaf persons, there is an absence or destruction of the hair cells. A cochlear implant 120 is utilized to directly stimulate the ganglion cells to provide a hearing sensation to the recipient.

FIG. 1 also shows how a cochlear implant 120 is positioned in relation to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises several components including a plurality of audio sensors spatially arranged on external components 122 of cochlear implant 120 for detecting sound. The spatial arrangement of the plurality of audio sensors is described in greater detail below.

Sound processor 126 is a directional sound processor configured to generate coded stimulation control signals representing sound detected by the plurality of audio sensors from a desired direction. These coded signals are then provided to an external transmitter unit 128. In the embodiment shown in FIG. 1, sound processor 126 is a behind the ear (BTE) sound processing unit. The BTE is constructed and arranged so that it can fit behind the outer ear 101 of a recipient. BTE may include a power source to power all elements of the cochlear implant, such as the external coil. In certain embodiments, the power source may be physically disconnected from the BTE, thereby causing the BTE to discontinue operation. Furthermore, in other embodiments, accessories can be connected to the BTE to add additional functionality. It should be appreciated by one of ordinary skill in the art that sound processor 126 may also comprise a body-worn sound processor, a modular sound processor or any type of sound processor now or later developed.

External transmitter unit 128 comprises an external coil 130 and, preferably, a magnet (not shown) secured directly or indirectly in external coil 130. External transmitter unit 128 is configured to transmit the coded signals from sound processor 126, along with power from a power source 129 such as a battery to internal components 124 through tissue 152.

Internal components 124 comprise an internal receiver unit 132 having an internal coil (not shown) that receives and transmits power and coded signals received from external assembly 122 to a stimulator unit 134 to apply the coded signal to cochlear 115 via an implanted electrode assembly 140. Electrode assembly 140 enters cochlea 115 at cochleostomy region 142 and has one or more electrodes 150 positioned to be substantially aligned with portions of tonotopically-mapped cochlea 115. Signals generated by stimulator unit 134 are typically applied by an array 144 of electrodes 150 to cochlea 115, thereby stimulating auditory nerve 116.

Because the cochlea is tonotopically mapped, that is, partitioned into regions each responsive to stimulus signals in a particular frequency range, each electrode of the implantable electrode array delivers a stimulating signal to a particular region of the cochlea. In the conversion of sound to electrical stimulation, frequencies are allocated to individual electrodes of the electrode assembly that lie in positions in the cochlea that are close to the region that would naturally be stimulated in normal hearing. This enables the cochlear implant to bypass the hair cells in the cochlea to directly deliver electrical stimulation to auditory nerve fibers, thereby allowing the brain to perceive hearing sensations resembling natural hearing sensations.

Figure 1B:
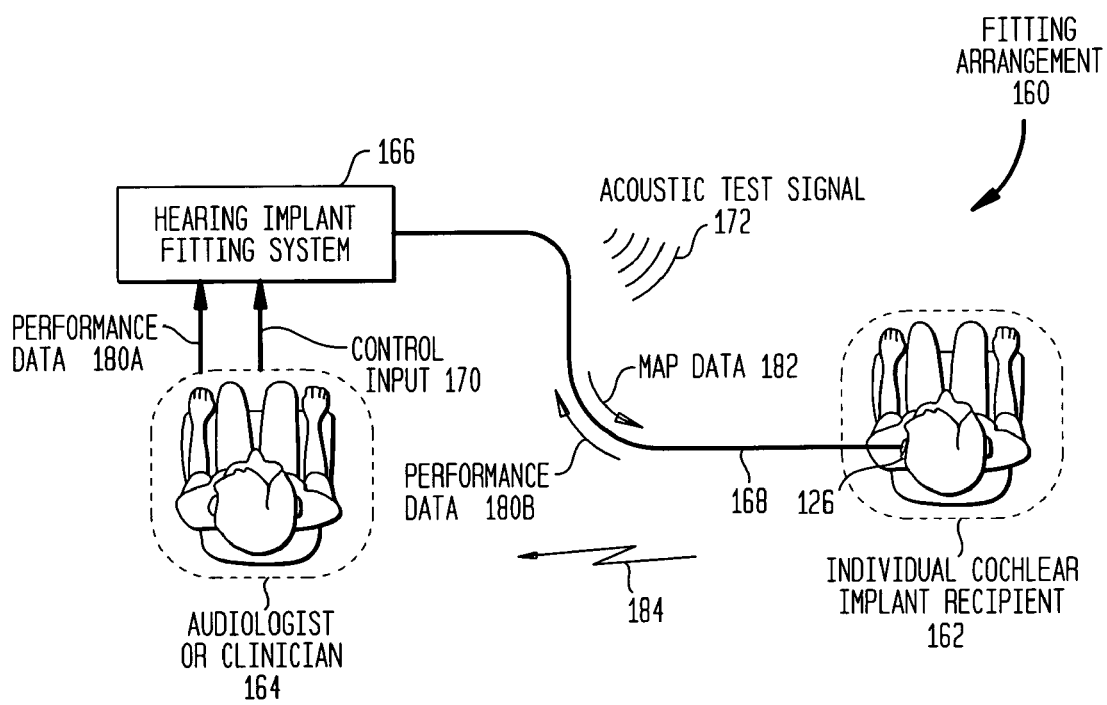
FIG. 1B is a schematic diagram illustrating one exemplary cochlear implant fitting arrangement configured to fit a cochlear implant to a recipient.

The effectiveness of a prosthetic hearing implant is dependent, not only on the device itself, but also on the way in which the device is configured or "fit" for the recipient. Fitting of a device, also referred to as "programming" or "mapping," creates a set of instructions that defines the specific characteristics used to stimulate the electrodes of the implanted array. This set of instructions is referred to as the recipient's "program" or "map." FIG. 1B is a schematic diagram illustrating one exemplary arrangement 160 in which a fitting system 166 is utilized to fit cochlear implant 120 to a recipient 162. As one of ordinary skill in the art would appreciate, the characteristics and code transmitted by cochlear implant 120 are dependent in part on the effectiveness with which the implant is fit to an individual recipient 162.

As noted, remotely distributed medical apparatus may include medical equipment associated with one or more portable medical devices. Such medical equipment includes, for example, medical equipment for implanting, maintaining, programming or otherwise servicing medical devices. In the exemplary application of a cochlear implant, such associated medical device may be, for example, a hearing implant fitting system.

As shown in FIG. 1B, an audiologist or clinician 164 uses a hearing implant fitting system 166 ("fitting system" herein) comprising interactive software and computer hardware to create individualized recipient map data 182 that are digitally stored on system 166 and ultimately downloaded to the memory of speech processor 126 of recipient 162. System 166 is programmed and/or implements software programmed to carry out one or more of the functions of mapping, neural response measuring, acoustic stimulating, and recording of neural response measurements and other stimuli.

In the embodiment illustrated in FIG. 1B, speech processor 126 of cochlear implant 120 is connected directly to fitting system 166 to establish a data communication link 168 between the speech processor and fitting system. System 166 is thereafter bi-directionally coupled by means of data communication link 168 with speech processor 126. It should be appreciated that although speech processor 126 and fitting system 166 are connected via a cable in FIG. 1B, any communications link now or later developed may be utilized to communicably couple the implant and fitting system.

Once cochlear implant 120 is calibrated, specific mapping data 182 is determined. The particular details of the implemented fitting process are specific to the recipient, cochlear implant manufacturer, cochlear implant device, etc. As a result, only selected exemplary mapping data are described herein for clarity.

Today, most cochlear implants require at least two values to be set for each stimulating electrode 150. These values are referred to as the Threshold level (commonly referred to as the "THR" or "T-level;" "threshold level" herein) and the Maximum Comfortable Loudness level (commonly referred to as the Most Comfortable Loudness level, "MCL," "M-level," or "C;" simply "comfort level" herein). Threshold levels are comparable to acoustic threshold levels; comfort levels indicate the level at which a sound is loud but comfortable. It should be appreciated that although the terminology and abbreviations are device-specific, the general purpose of threshold and comfort levels is common among all cochlear implants: to determine a recipient's electrical dynamic range.

In adult cochlear implant patients, threshold and comfort levels are typically measured using verbal feedback from recipient 162. For children, who often lack the listening experience, language, or conceptual development to perform specific fitting tasks, audiologists and clinicians must often rely on clinical intuition and trial and error to appropriately estimate comfort levels for young recipients. The above and other feedback is generally referred to by reference numeral 184 in FIG. 1B. Performance data provided directly to fitting system 166 may be provided via data connection 168 as performance data 180B, while performance data provided by the audiologist/clinician based on oral feedback or observations 184 is shown in FIG. 1B as performance data 180A (performance data 180A and 180B are generally and collectively referred to herein as performance data 180).

As noted, in aspects of the present invention operational data is automatically collected from remotely distributed medical apparatus which include portable medical devices and associated medical equipment. In an exemplary application of a prosthetic hearing device, then, the term "medical apparatus" refers to a cochlear implant 120, hearing implant fitting system 166, as well as any other equipment for implanting, maintaining, programming or otherwise servicing the cochlear implant, referred to as "cochlear implant equipment" herein. It should be appreciated, then, that reference to cochlear implant 120 and fitting system 166 is also applicable to other types of medical devices and associated medical equipment where consistent and unless stated otherwise.

The operational data automatically collected from cochlear implant 120, fitting system 166, or other cochlear implant equipment includes, but is not limited to, performance data of hardware and software components, exception data generated by hardware and/or software components, and other data related to cochlear implant 120, fitting system 166, or other cochlear implant equipment.

The captured operational data may also include patient-related data such as MAP data 182, monitored physiological parameters, device settings, and other data indicating how a user chooses to operate cochlear implant 120, fitting system 166, or other cochlear implant equipment (hereinafter, "usage information"). Usage information may also include the extent and frequency of use of software functions of cochlear implant 120, fitting system 166, or other cochlear implant equipment, speech processing strategies used in cochlear implant 120, time spent using each panel of fitting system 166, or other cochlear implant equipment, number of clicks per button of a fitting system 166, or other cochlear implant equipment, number of calls per function of a fitting system 166, or other cochlear implant equipment, etc. Usage data includes, but is not limited to, the frequency of use of particular user parameters implemented by a clinic, the success of particular user parameters implemented, changes in a user's user parameters or speech processing strategy between visits to the clinic, etc.

The captured operational data may also include technical data such as battery life, current or voltage requirements, battery charge times, version and configuration of the hardware and/or software components of cochlear implant 120, speech processing information, execution speed or platforms of hardware or software, etc.

It would be appreciated by one of ordinary skill in the art that the present invention may be used to capture operational data from the particular distributed medical apparatus may be different than that noted above.

Figure 2:
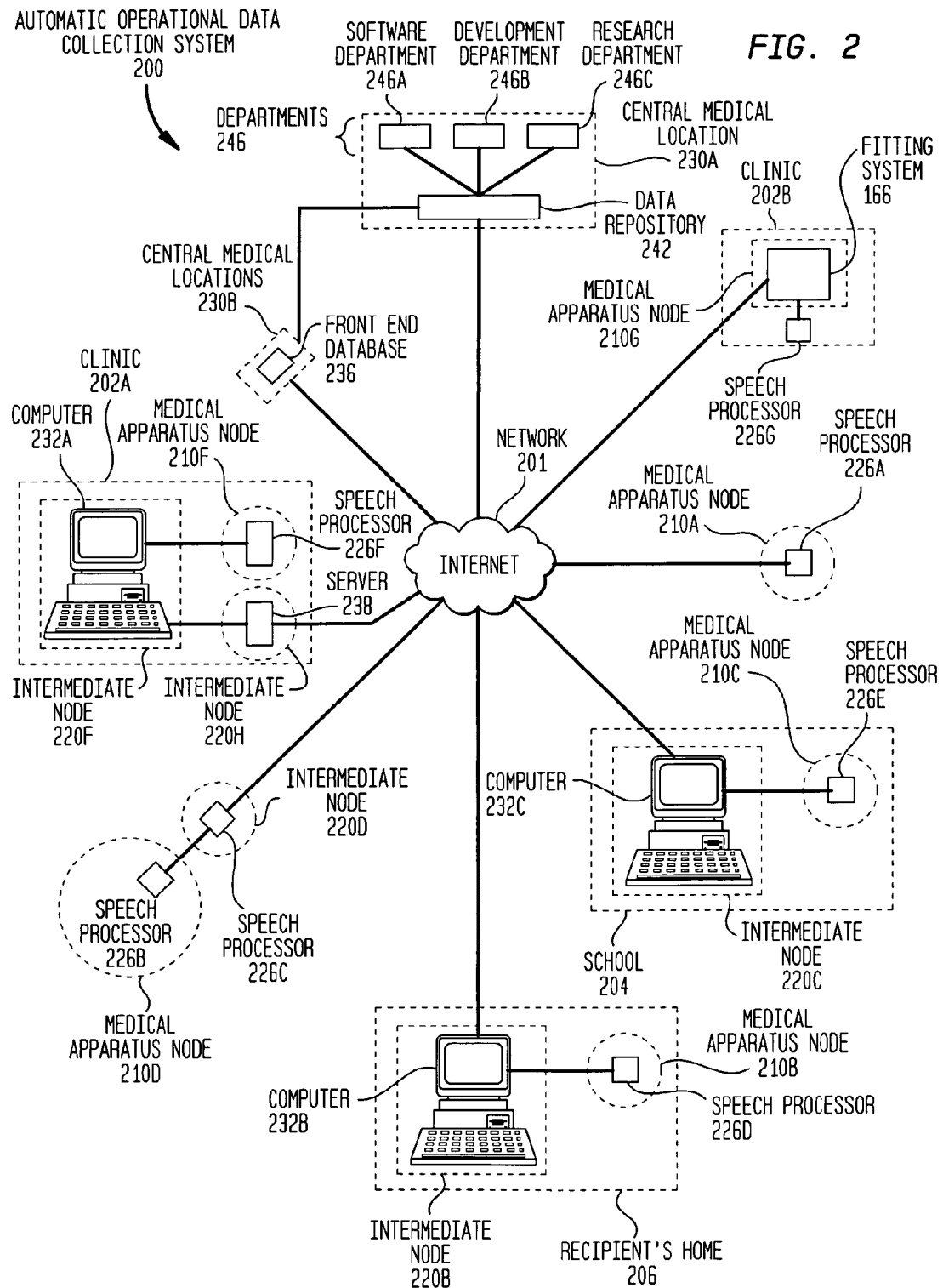
FIG. 2 is a block diagram illustrating an exemplary network for the capture, collection and distribution of operational data from remotely distributed medical apparatus, in accordance with certain embodiments of the present invention.

Turning to embodiments of the present invention, FIG. 2 is an illustration of an exemplary network for the capture, collection and distribution of operational data, in accordance with certain embodiments of the present invention. As noted, operational data is transferred from remotely distributed medical apparatus to the medical device operational data repository via any network now or later developed. In the exemplary application illustrated in FIG. 2, the network is a computer network, namely, the Internet.

In FIG. 2, a plurality of remotely distributed medical apparatus nodes 210 are shown. Medical apparatus nodes 210 are each configured to capture operational data and transmit the operational data to a data repository 242 located in a central medical location 230 via network 201. In the embodiments of the present invention shown in FIG. 2, medical apparatus nodes 210 transmit operational data to central medical location 230 at least partially via an internet network. Details of medical apparatus nodes 210 are described in detail below.

In one scenario, a medical apparatus node 210A comprises a speech processor 226A. As shown in FIG. 2, speech processor 226A is referred to as a medical apparatus node 210A in this exemplary network 201. Speech processor 226A automatically captures operational data and determines that the speech processor has direct internet access to data repository 242 at central medical location 230A; that is, there are no intermediate nodes on the determined route. As such, speech processor 226A may determine that the most efficient route over which the operational data is to be transferred to data repository 242 is via this direct internet connection. In such circumstances, speech processor 226A automatically transmits the operational data to data repository 242 via the determined route.

In another scenario illustrated in FIG. 2, a medical apparatus node 210C comprises a speech processor 226E. Speech processor 226E automatically captures operational data and determines that the speech processor does not have direct internet access to data repository 242 in central medical location 230A. Due to this lack of direct internet access, speech processor 226E must determine a route over which to transfer the operational data that involves one or more intermediate nodes. For example, speech processor 226E may determine that the transfer of operational data to intermediate node 220C would be the most efficient route for the operational data to be transmitted to data repository 242. Speech processor 226E automatically establishes a communication link with intermediate node 220C and transmits the operational data to intermediate node 220C via a network connection.

After receipt of the operational data, intermediate node 220C determines that direct internet access to data repository 242 is available. Intermediate node 220C then transmits the operational data received from speech processor 226E to data repository 242 in central medical location 230 via this direct network route through the Internet 201. In this exemplary embodiment, intermediate node 220C is located, for example, at a school 204. Such as school may be, for example, a training facility in which the recipient is trained to use a cochlear implant that includes speech processor 226E. In such a school, intermediate node 220C may be embodied, for example, in a conventional desktop or other computer 232C configured to perform operations associated with the training of the recipient. Alternatively, school 204 is an academic institution. Regardless, computer 232C is configured in accordance with the teachings of the present invention to perform the operations of an intermediate node. Details of exemplary embodiments of an intermediate node 232 are described in detail below.

In another scenario illustrated in FIG. 2, a speech processor 226D, referred to as medical apparatus node 210B, is configured in accordance with the teachings of the present invention to automatically capture operational data and to determine a desired route through Internet 201 to data repository 242. In this scenario, speech processor 226E automatically establishes a communication link with intermediate node 220B located in the recipient's home 206. In this embodiment, computer 238 is a conventional desktop, laptop or the like configured in accordance with the teachings of the present invention to perform operations of an intermediate node 220 described in detail below.

In yet another scenario shown in FIG. 2, a medical apparatus node 210D comprising a speech processor 226C. Similar to the noted speech processors 226E and 226D, speech processor 226B is configured to automatically capture selected operational data, and to determine a route through Internet 201 to data repository 242. In this example, speech processor 226B determines that the desired route for the operational data to data repository 242 is through intermediate node 220D. In this example, intermediate node 220D comprises another speech processor 226C. Speech processor 226B transmits the operational data to speech processor 226C via a network connection, and speech processor 226C transmits the operational data to data repository 242 via internet 201. In other words, portable medical devices may be configured as a medical apparatus node 210 or as an intermediate node 220. This is described in greater detail below.

In a still other scenario shown in FIG. 2, a medical apparatus node 210F comprises a speech processor 226F that does not have direct internet access to data repository 242. Speech processor 226F automatically determines that a desired route for the operational data to data repository 242 is through intermediate node 220F. Intermediate node 220F comprises a computer 232A at a clinic 202A. Computer 232A may be, for example, a fitting system such as that described above with reference to FIG. 1B. Speech processor 226F transmits the operational data to computer 232A via a network connection. In this exemplary scenario, computer 232A also does not have direct internet access to data repository 242. As a result, computer 232A determines a route for the operational data to data repository 242 is through an intermediate node 220H. Intermediate node 220H comprises, in this example, a server 238 located for example at clinic 202A. Server 238 has direct internet access to data repository 242 and transmits the operational data to data repository 242 via the direct internet connection.

In a further scenario shown in FIG. 2, a clinic 202B has a fitting system 166 configured as medical apparatus node 210G. As noted above with reference to FIG. 1B, fitting system 166 is configured to be used to fit speech processor 226G for a recipient. In this scenario, fitting system 166, which has direct internet access to data repository 242, generates the operational data to be provided to data repository 242 in addition to or as an alternative to capturing operational data from speech processor 226G. As such, fitting system 166 automatically transmits the operational data to data repository 242 via the internet.

FIG. 2 illustrates two different embodiments of a central medical location 230, central medical location 230A and central medical location 230B. In a first embodiment, central medical location 230A comprises a server 242 that serves as the data repository. As such, server 242 receives the operational data from the remotely distributed medical apparatus nodes 210. Server 242 may, for example, filter the received operational data and distribute relevant portions of such data to departments 246 for analysis. For instance, a software development department 246A may receive a weekly update of all new anomalies reported per application or per release. In addition, reports may be generated for a development department 246B. Other information can be obtained as needed, such as by a research department 246C.

In a second embodiment, central medical location 230B comprises a front end database 236 that receives operational data from one or more distributed medical apparatus nodes 210. In this embodiment, central medical location 230B acts a local central medical location and transmits the received operational data to a second location for analysis and distribution. In the embodiment shown, front end database 236 transmits the received operational data to server 242 for distribution.

It should be appreciated by one of ordinary skill in the art that connections between medical apparatus nodes 210 and intermediate nodes 220 are not limited to any specific type of connection, and may be made by any hardware or wireless connections, including, but not limited to, RF connection, local area network connection, wide-area network connection, and the like, a telephone network connection, or other connection regardless of transmission medium.

Furthermore, the above embodiments have been described with reference to an internet network, but it would be appreciated by one of ordinary skill in the art that the embodiments may perform equally well with other previously identified types of networks, and the operational data may be transmitted via internet email, http, SOAP, IRC, ftp, instant message, .net framework, traditional fax or with a barcode describing the captured operational data, traditional telephone and modem and mobile phone SMS message.

It would also be appreciated by one of ordinary skill in the art that medical apparatus nodes 210 may use any number of intermediate nodes 220 to efficiently route operational data to central medical location 230.

Figure 3:
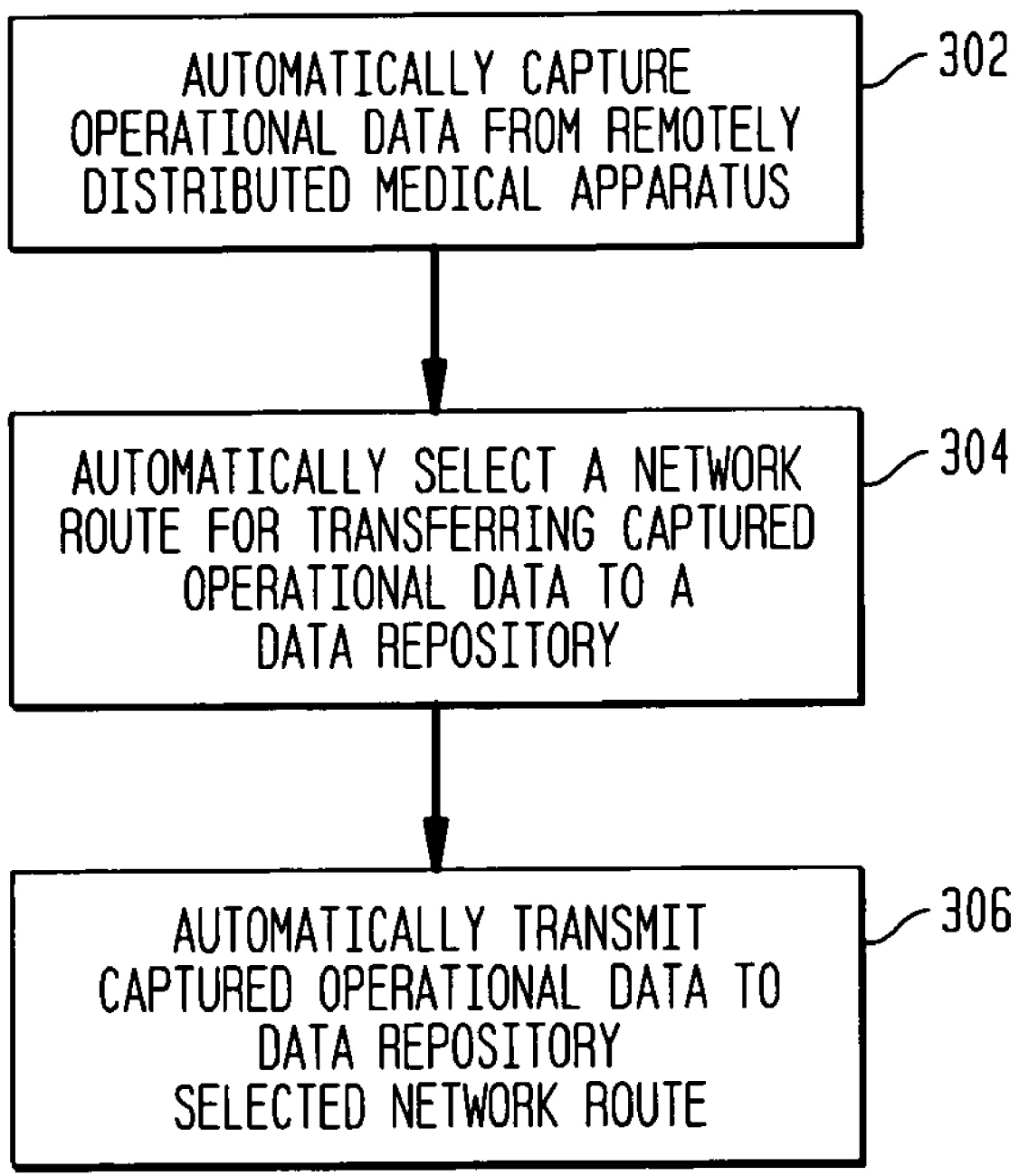
FIG. 3 is a high level flowchart illustrating the general aspects of the collection of operational data in accordance with embodiments of the present invention.

Referring to more general aspects of the present invention, FIG. 3 is a flowchart illustrating the operations performed to capture and collect selected operation data from distributed medical apparatus. At block 302 the operational data is automatically captured from a remote medical apparatus. At block 304, a route over a network communicably coupling the medical apparatus and a data repository is determined. The operational data is then transmitted from the remote medical apparatus to the data repository over the selected network route, as shown at block 306. The collocated operational data is stored at the data repository for real-time or subsequent review and analysis.

Figure 4:
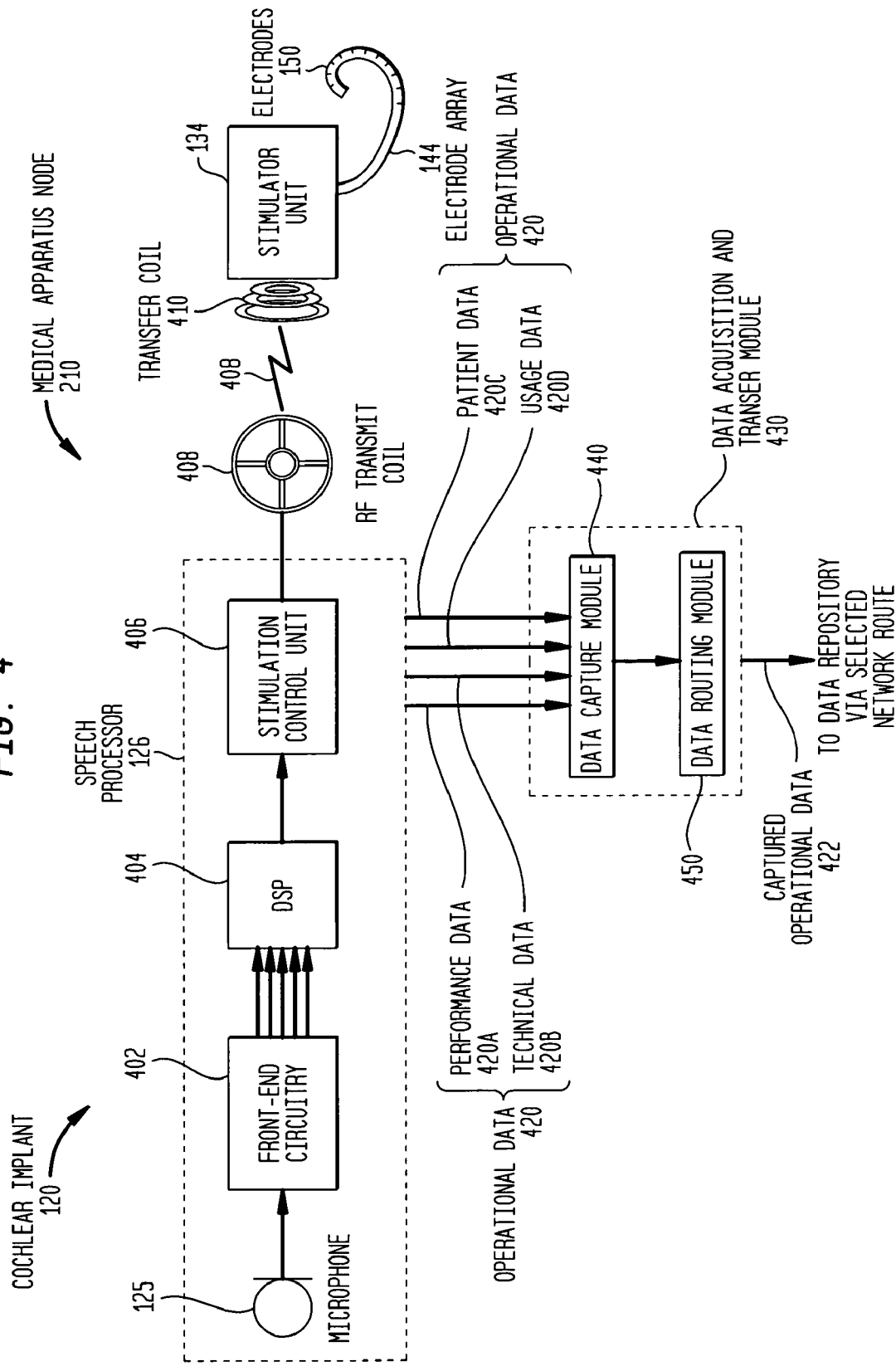
FIG. 4 is a functional block diagram illustrating a medical apparatus node in accordance with embodiments of the present invention.

FIG. 4 illustrates one embodiment of medical apparatus node 210. In this embodiment, medical apparatus node 210 is the portable medical device introduced above, namely cochlear implant 120. Cochlear implant 120 comprises a speech processor 126, external transcutaneous transmit coil 130, internal transcutaneous transfer coil 410, implantable stimulator unit 134 that electrically stimulates cochlea 115 via electrodes 150 disposed on elongate electrode array 144. In accordance with embodiments of the present invention, medical apparatus node 210 further comprises a data acquisition and transfer module 430 in or operationally connected to cochlear implant 120. For ease of description, data acquisition and transfer module 430 will be referred to as being "in" cochlear implant 120 or other medical apparatus 210.

Speech processor 126 includes microphone 125 for detecting sound waves 107 and generating an analog audio signal responsive to a received acoustic wave 107, front-end circuitry to that generates a series of band-pass filtered digital signals, and a digital signal processor (DSP) 404. DSP 304 detects instantaneous energy of the audio signal in the frequency range of each of the series of band-pass filtered signals. DSP 304 may select a number of maxima (i.e., the channels having the largest amplitude) in accordance with one of a variety of speech processing techniques such as the Spectral PEAK Extraction (SPEAK) or Advanced Combination Encoders (ACE) speech coding strategies. Stimulation control unit 406 receives the filter channel signals (or selected maxima) and stimulation rate information and determines the signals for stimulating electrodes 150 of electrode array 144, including the rate of stimulation, the group of electrodes to be stimulated, and the current amplitude for stimulating the electrodes. The received information is mapped to electrodes 150 of electrode array 144 to generate a stimulus current level for each stimulus to be applied in accordance with stimulus pulse timings. External coil 130 transmits this information to internal coil 410 which then provides the information to stimulator unit 134 for stimulation of cochlea 115. The function and operation of cochlear implant 120 is exemplary only and is well-known in the art.

As noted, further included in medical apparatus node 210 is a data acquisition and transfer module 430. Data acquisition and transfer module 430 comprises a data capture module 440 and a data routing module 450. Data capture module 440 captures one or more of performance data 420A, technical data 420B, patient data 420C and usage data 420D (collectively and generally referred to herein as "operational data 420"). Data capture module 440 converts operational data 420 as necessary to a format suitable for transmission over the network, for example, network 201 (FIG. 2). The formatted operational data 422 is provided to a data routing module 450 described below with reference to FIG. 6. Data routing module 450 determines a desired route for operational data 420 to data repository 242 located at central medical location 230. Data routing module 450 then transmits captured operational data 422 to an next node of network 201. That next node may be data repository 242 or an intermediate node 220 as described above. Details of data routing module are described below with reference to FIG. 7.

Figure 5:
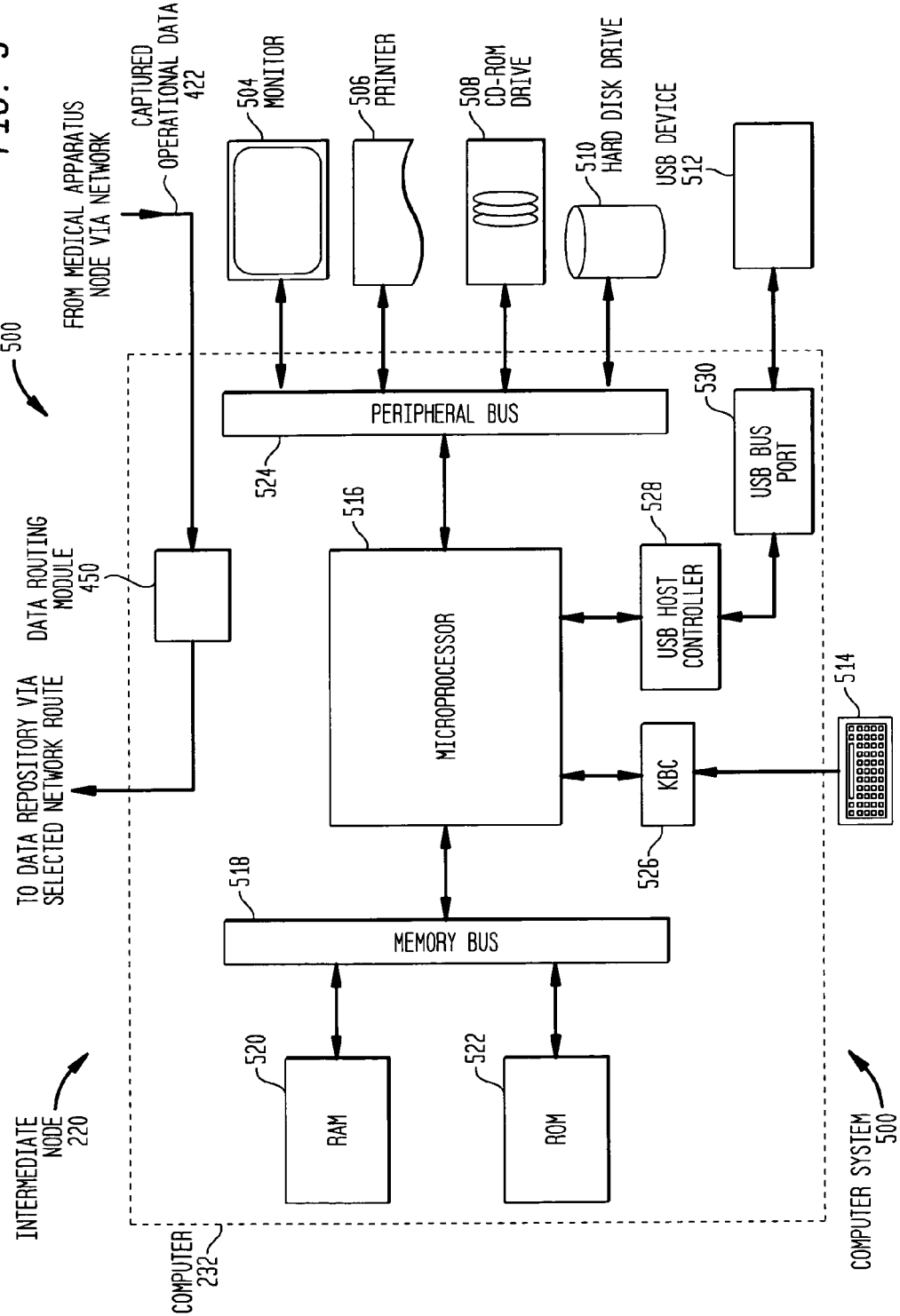
FIG. 5 is a functional block diagram illustrating an intermediate node in accordance with embodiments of the present invention.

FIG. 5 is a functional block diagram illustrating one embodiment of an intermediate node 220 of FIG. 2. As shown in FIG. 5, intermediate node 220 comprises a computer system 500. Computer system 500 may include, for example, a computer 232, a display screen or monitor 504, a printer 506, a CD-ROM drive 508, a hard disk drive 510, a USB device 512 and a keyboard 714. Computer 232 includes a microprocessor 516, a memory bus 518, a random access memory (RAM) 520, read only memory (ROM) 522, a peripheral bus 524, a keyboard controller 526, a USB host controller 528, a USB bus port 530 and a data routing module 440A.

Computer system 500 functions similar to conventional personal computers and, therefore, is not described further herein. In accordance with the teachings of the present invention, computer system 500 also includes a data routing module 450A. Data routing module 450 enables computer system 500 to operate as an intermediate node 220 as described above with reference to FIG. 2. In the embodiment shown, data routing module 450 receives formatted operational data 422 from a medical apparatus node 210. Data routing module 450 determines a route for operational data 422 and transmits captured operational data 422 to data repository 242 in central medical location 230 via the selected network route. As will be apparent to those of ordinary skill in the art, data routing module 450 in intermediate node 220 (FIG. 5) and portable medical apparatus node 210 (FIG. 4) may implement the same or different routing algorithm. As noted above, details of data routing module 450 are described below with reference to FIG. 7.

Figure 6:
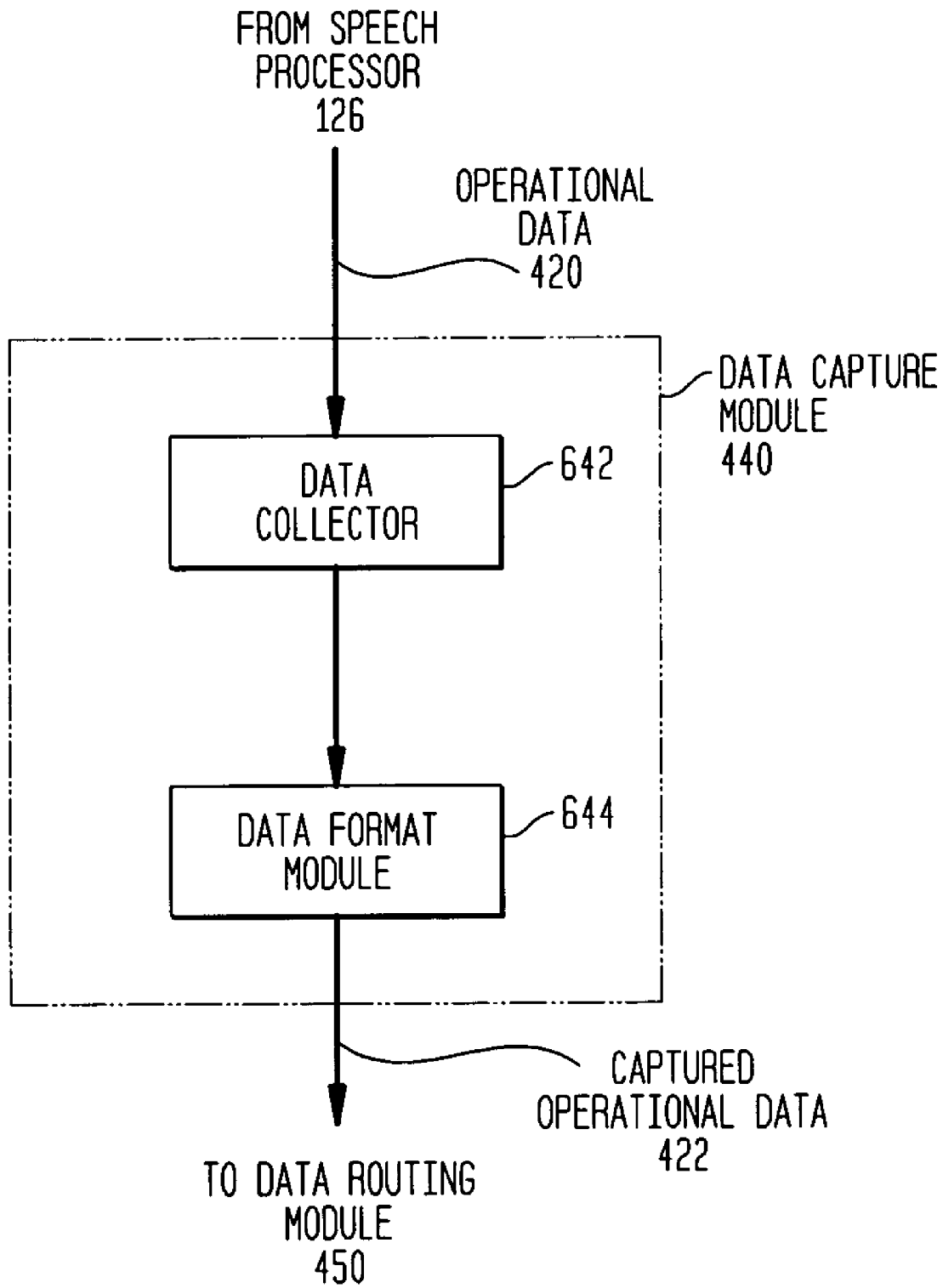
FIG. 6 is a functional block diagram illustrating one embodiment of the data capture module shown in FIG. 4.

FIG. 6 is a functional block diagram illustrating one embodiment of data capture module 440 introduced above with reference to FIG. 4. Data capture module 440 comprises a data collector 642 and a data format module 644. In the embodiment shown, data collector 642 acquires operational data 420 from speech processor 126. As would be appreciated by one of ordinary skill in the art, data collector 642 may be any active or passive device capable of acquiring data. In certain embodiments, data collector 642 interrogates speech processor 126 to acquire operational data 420 while in other embodiments speech processor 126 provides operational data 420 to data collector 642 without a request by data collector 642.

In certain embodiments, operational data 420 acquired by data collector 642 may not be in a format suitable for transmission over network 201. In such embodiments, data format module 644 is implemented to receive the captured operational data from data collector 642 and to convert the operational data to an appropriate format. It should be appreciated by those of ordinary skill in the art that the term "format" refers to any characteristic of operational data 420 that may be manipulated to effect transmission of the implemented network 201. Such manipulations are anticipated to accommodate the application or presentation network levels of the Open Systems Interconnect (OSI) Reference Model, but may include operations more commonly associated with other such network levels such as the session, transport, network data link or physical layers. (The OSI model is a well-known model established by the International Standards Organization (ISO) to standardize protocols connecting open systems.) As is well known to those in the art, medical apparatus node 210 includes other components not shown that perform such various operations to enable medical apparatus 210 to function as a node on network 210. As such, the formatting of operational data 420 performed by data format module 644 is likely to be limited to those operations more commonly associated with the application or presentation level of the OSI Reference Model.

In one embodiment, data format module 644 converts operational data 420 from is source format to a human-readable text format such as eXtensible Markup Language (XML). XML is a subset of Standard Generalized Markup Language (SGML) that is more powerful and flexible than Hypertext Markup Language (HTML). XML provides a common syntax for expressing structure in data. Structured data refers to data that is tagged for its content, meaning, or use. XML provides an expansion of the tagging that is done in HTML, which focuses on format or presentation. XML tags identify XML elements and attributes of XML elements. XML elements can be nested to form hierarchies of elements. Also, formatted operational data 422 may be viewed in any text editor and easily passed around the World Wide Web (WWW) by using text-based protocols such as Hypertext Transfer Protocol (HTTP), for example.

In certain embodiments, data form module 644, as part of the "formatting" operations that it performs, may also add data to facilitate the storage of data at data repository 242. For example, in one embodiment, data format module 644 encodes operational data 420 to further include information that uniquely identifies medical apparatus node 210, the type of medical apparatus node 210, timestamp data, and other similar information.

Figure 7:
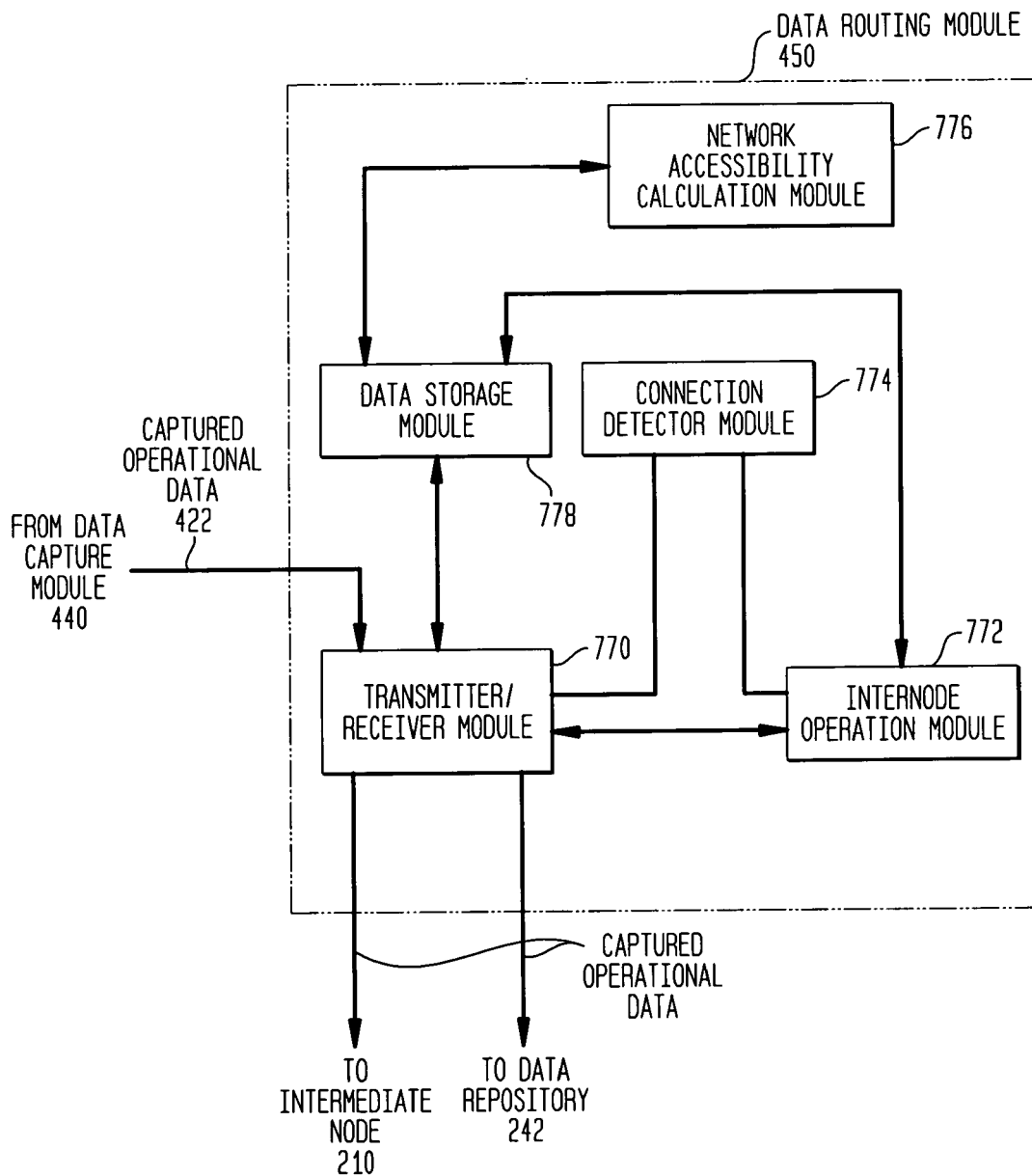
FIG. 7 is a functional block diagram illustrating one embodiment of the data routing module shown in FIG. 4.

As noted above, data capture module 440 transmits formatted operational data 422 to data routing module 450. FIG. 7 is a functional block diagram of one embodiment of data routing module 450. Data routing module 450 comprises a transmitter/receiver module 700, an internode operation module 772, a connection detection module 774, an network accessibility calculation module 776 and a data storage module 778.

Network accessibility calculation module 776 calculates a numerical representation of the network accessibility of data routing module 450 and stores this representation into data storage module 778. Details of this calculation are provided below with reference to FIG. 11C.

Transmitter/receiver module 770 receives formatted operational data 422 from data capture module 440 and stores the formatted operational data 422 in data storage module 778. Connection detector module 744 determines if any network connections are available to medical apparatus node 210. In accordance with embodiments illustrated in FIG. 2, if connection detector module 774 determines that a direct internet connection to data repository 242 is available, connection detector module 774 alerts transmitter/receiver module 700 of this direct network connection. Transmitter/receiver module 700 retrieves formatted operational data 422 from data storage module 778 and transmits formatted operational data 422 to data repository 242 via the network connection.

As would be appreciated by one of ordinary skill in the art, transmitter/receiver module 770 does not necessarily actively retrieve the formatted operational data from data storage module 778. Rather, if a direct internet connection is available to medical apparatus node 210, data storage module 778 may provide stored operational data 422 to transmitter/receiver module 700 without active participation on the part of transmitter/receiver module 770.

In accordance with other embodiments, connection detector 774 does not detect a direct network connection between medical apparatus node 210 and central medical location 230. In such embodiments, connection detector 774 checks the availability of a network connection between medical apparatus node 210 and an intermediate node 220. If connection detector module 774 determines that a connection to an intermediate node 220 is available, connection detector module 774 alerts internode operational module 772.

Figure 9:
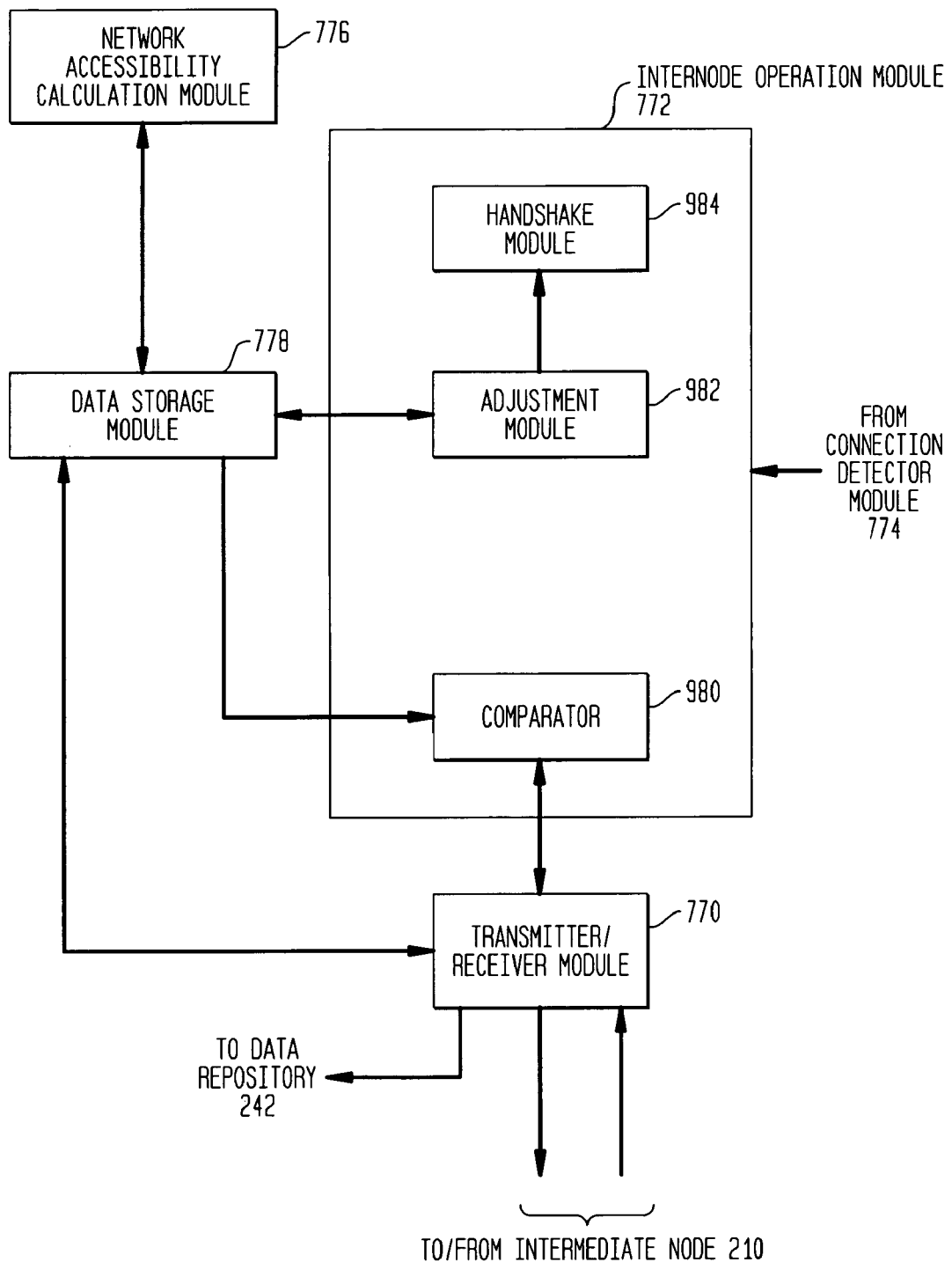
FIG. 9 is a functional block diagram illustrating one embodiment of the internode operation module shown in FIG. 7.

Upon notification, internode operational module 772 determines if formatted operational data 422 should be transferred to detected intermediate node 220 or if medical apparatus node 210 should receive additional operational data from detected intermediate node 220. Internode operation module 772 then instructs transmitter/module 770 to either transmit formatted operational data 422 stored in data storage module 778 to intermediate node 220 or receive additional operational data from intermediate node 220. Details of internode operational module 772 are described below with reference to FIG. 9.

In other embodiments, after data routing module 450 receives formatted operational data 422, connection detector module 774 determines that there is no connection available. In such a circumstance, data routing module 450 waits until a connection becomes available. Connection detector module 774 may periodically search for a connection periodically or continually until an available connection is found.

As would be appreciated by one of ordinary skill in the art, in alternative embodiments, transmitter/receiver module 700 does not store captured operational data in data storage module before connection detector module 774 determines if connections are available. In such embodiments, if connection detector module 774 determines a direct internet connection between medical apparatus node 210 and data repository 242 is available, transmitter/receiver module 770 may transmit formatted operational data 422 to data repository 242 without requiring storage in data storage module 778.

Figure 8A:
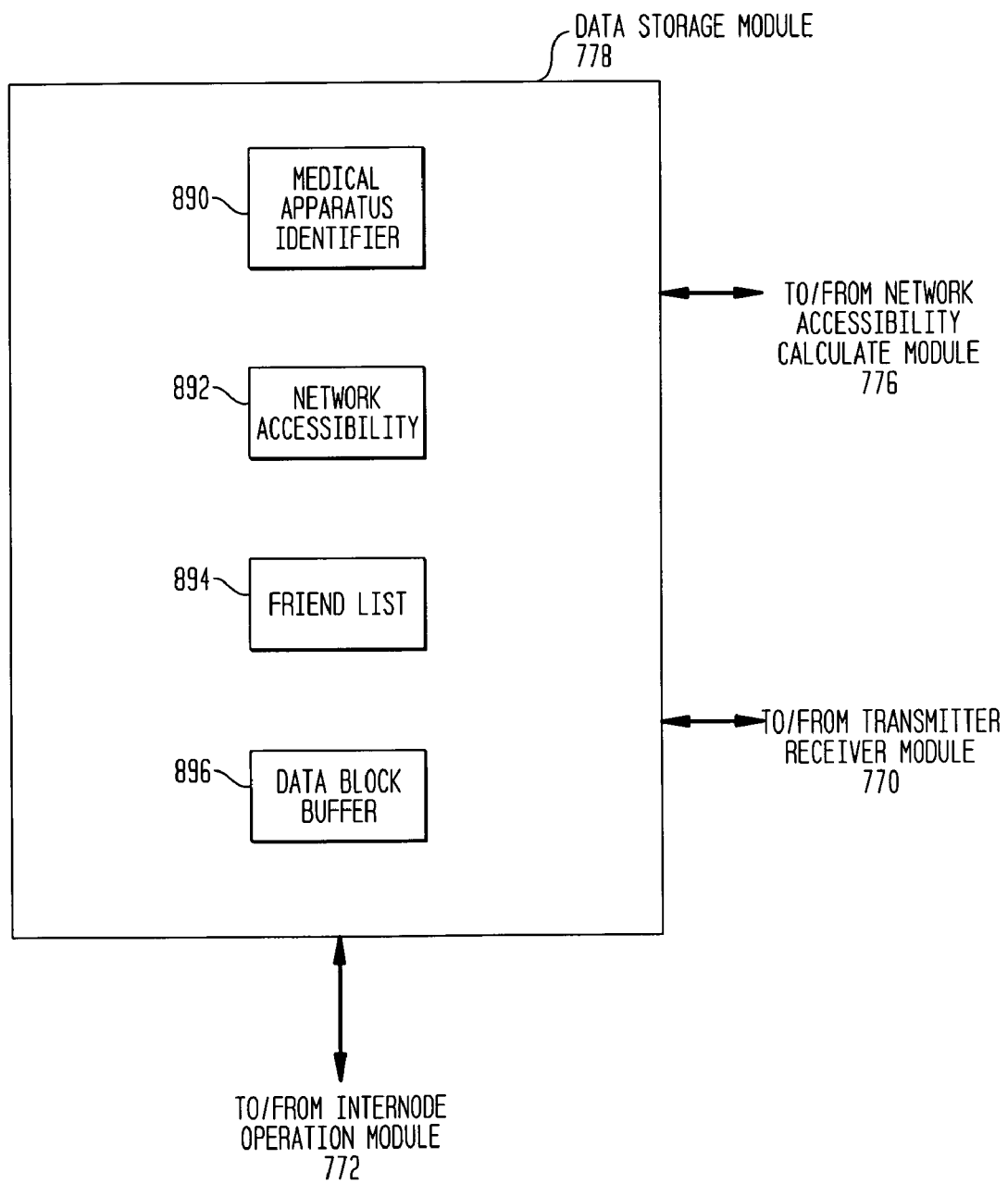
FIG. 8A is a functional block diagram illustrating one embodiment of the data storage module shown in FIG. 7.

FIG. 8A is a functional block diagram illustrating one embodiment of data storage module 778. Stored in data storage module 778 is a medical apparatus identifier 890, and a representation of network accessibility, referred to as internet accessibility 892 since exemplary network 201 is the Internet. Stored in data storage module 778 is a friend list 894, and a data block buffer 896. Data storage module 778 is in communication with network accessibility module 776, transmitter/receiver module 770 and internode operation module 772.

Medical apparatus identifier 890 is an identifier that is specific to medical apparatus node 210. Each medical apparatus node or intermediate node in system 200 has a medical apparatus identifier that is unique to that node. In certain embodiments, formatted operational data 422 is encoded with medical apparatus identifier 890 corresponding to medical apparatus node 210 during the XML formatting described above with reference to FIG. 6.

Data block buffer 896 is a buffer of memory that stores formatted operational data 422 received from data capture module 440 and intermediate nodes 220.

Friend list 894 has stored therein properties of certain intermediate nodes 220 that medical apparatus node 210 has formed a connections with. These certain nodes that medical apparatus node has connected with are referred to as friends of medical apparatus node 210. Details of friend list 894 are described below with reference to FIG. 8B.

Internet accessibility 892 is a representation of the amount of time that medical apparatus node 210 has a direct internet connection added to certain internet connection properties of friends of medical apparatus node 210. Details on the calculation of internet accessibility 892 are provided below with reference to FIG. 11C.

FIG. 8B is an exemplary view of one embodiment of friend list 894 shown in FIG. 8A. As noted above, friend list 894 has stored therein properties of each friend of medical apparatus node 210. In the illustrated embodiment, friend list 894 stores a medical apparatus identifier 891, internet accessibility 893, friend accessibility 895, friend-internet accessibility 897 and a remark 899 for each friend of medical apparatus node 210.

As noted above, medical apparatus identifiers 891 are representations that are unique for each friend of medical apparatus node 210. Similar to internet accessibility 892 of medical apparatus node 210, each internet accessibility 893 is a representation of the amount of time that the particular friend has a direct internet connection added to certain internet connection properties of nodes stored in its friend list. Friend accessibility 895 for each friend is a representation of the percentage of time that medical apparatus node 210 has the ability to connect to the particular friend. Friend-internet access 897 is a representation of the value of the particular friend to medical apparatus node 210 for transmitting formatted operational data 422 to central medical location 230. Details of these properties are provided below.

It would be appreciated by one of ordinary skill in the art that these stored properties are shown in chart form for ease of illustration and that friend list 894 may store the properties in various formats and arrangements. It would further be appreciated that friend list 894 may store more values or properties than those shown in FIG. 8B.

As noted above, FIG. 9 illustrates one embodiment of internode operation module 772. Internode operation module 772 comprises a handshake module 984, an adjustment module 982 and a comparator 980.

In the illustrated embodiment, connection detector module 774 alerts internode operation module 772 that a connection to intermediate node 220 is available. As such, handshake module 984 performs a handshake operation with intermediate node 220 via transmitter/receiver module 770 to verify that medical apparatus node 210 and intermediate node 220 are compatible.

In certain embodiments, if handshake module 984 determines that the nodes are not compatible, data connection module 774 searches for an alternative connection.

After a successful handshake operation, adjustment module 982 retrieves medical apparatus identifier 891, internet accessibility 893, friend accessibility 895, friend's internet accessibility 897 and remark 899 from intermediate node 220 via transmitter/receiver 770. Adjustment module 982 determines if intermediate node 220 is a member of friend list 894 of medical apparatus node 210. If intermediate node 220 is a member of friend list 894, adjustment module 982 updates friend list 894 to reflect any changes in the properties of intermediate node 220. If adjustment module 982 determines that intermediate node 220 is not a member of friend list 894, adjustment module 982 adds intermediate node 220 to friend list 894. Internet accessibility calculation module 776 updates internet accessibility 892 of medical apparatus node 210 to reflect any changes in friend list 894. Details on the process of adjusting friend list 894 are described below with reference to FIG. 11B.

Following update of friend list 894, comparator 980 compares internet accessibility 892 of medical apparatus node 210 to internet accessibility 893 of intermediate node 220. In certain embodiments, internet accessibility 892 is lower than internet accessibility 893 and comparator 980 instructs transmitter/receiver module 770 to send formatted operational data 422 stored in data block buffer 896 to intermediate node 220. Intermediate node 220 will receive formatted operational data 422 from medical apparatus node 210 until all operational data 422 stored in data block buffer 896 is transferred or the memory of intermediate node 220 is full. Medical apparatus node 210 continues operation and repeats the above process if additional data is captured.

In other embodiments, internet accessibility 892 of medical apparatus node 210 is higher than internet accessibility 893 of intermediate node 220. In these embodiments, comparator 980 instructs transmitter/receiver module 770 to receive any captured operational data stored in intermediate node 220. Medical apparatus node 210 will receive any operational data from intermediate node 220 until all operational data stored in intermediate node 220 is transferred or data block buffer 896 is full. In these embodiments, medical apparatus node 210 will continue to search for a connection to transmit the stored operational data to central medical location 230 until all the stored operational data has been transmitted. It would be appreciated that medical apparatus node 210 may search for a connection at certain time intervals or may continually search for a connection.

In preferred embodiments of the present invention, formatted operational data 422 is transferred to or from data block buffer 896 using a First In, First Out (FIFO) structure. It would be appreciated by one having ordinary skill in the art that the present invention could also use other data storage and transfer structures including know or later developed, such as Last In, First Out (LIFO).

Figure 10:
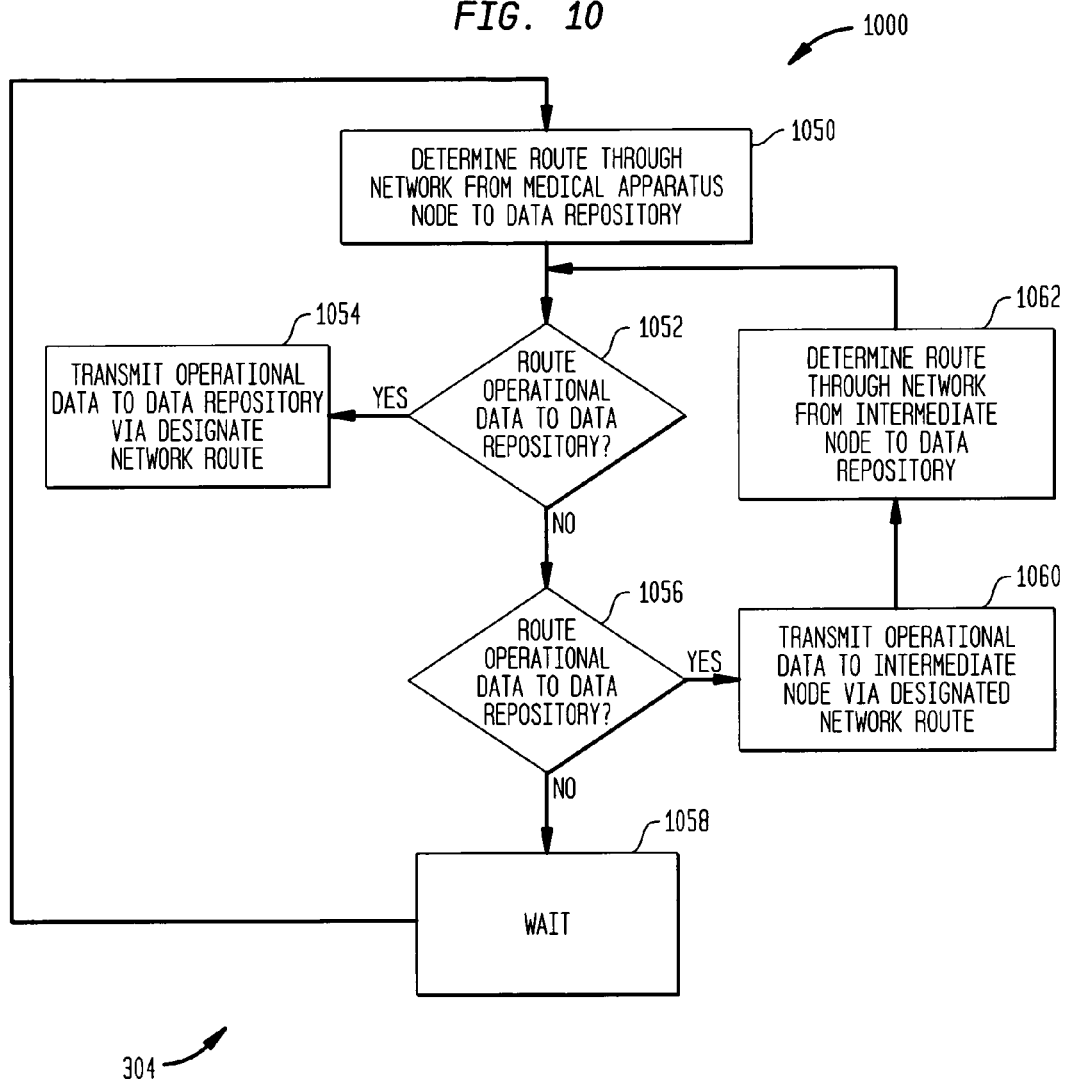
FIG. 10 is a flowchart illustrating one embodiment of the process of automatically transmitting operational data to the medical device operational data repository illustrated of FIG. 3.

FIG. 10 is a detailed flowchart illustrating one embodiment of a process 1000 of automatically transmitting formatted operational data 422 to data repository 242 of FIG. 3. At block 1050, a route for formatted operational data 422 from medical apparatus node 210 to data repository 242 through network 201 is determined. At block 1052, a determination is made if a direct network connection between medical apparatus node 210 and data repository 242 is available. If such a direct network connection is available, block 1054 transmits formatted operational data 422 to data repository 242 via this selected or designated network route using the direct network connection.

If at block 1052 a direct network connection is determined to not be available, processing advances to block 1056. At block 1056 a determination is made of whether a connection to an intermediate node 220 is available and if intermediate node 220 is the desired route for captured operational data 422. If no connection to an intermediate node 220 is available or if an available connection is not a desirable route for captured operational data 442, process 1000 waits at block 1058. Periodically process 1000 returns to block 1050 to reinitiate the selection of a network route for captured operational data 422.

Returning to block 1056, if a connection to an intermediate node 220 is available and is a desired route for captured operational data 422, captured operational data 422 is transmitted to intermediate node 220 via a selected network connection. At block 1062 process 1000 initiates a determination of route for captured operational data 422 from intermediate node 220 to data repository 242. Such a route may be selected based on one or more selection criteria including but no limited to, speed, safety of data, reliability, efficiency, etc. Process 1000 makes the above determinations at blocks 1052 and 1056 and continues transferring captured operational data 422 to other intermediate nodes until a direct network connection to data repository 242 is available and usable.

Figure 11A:
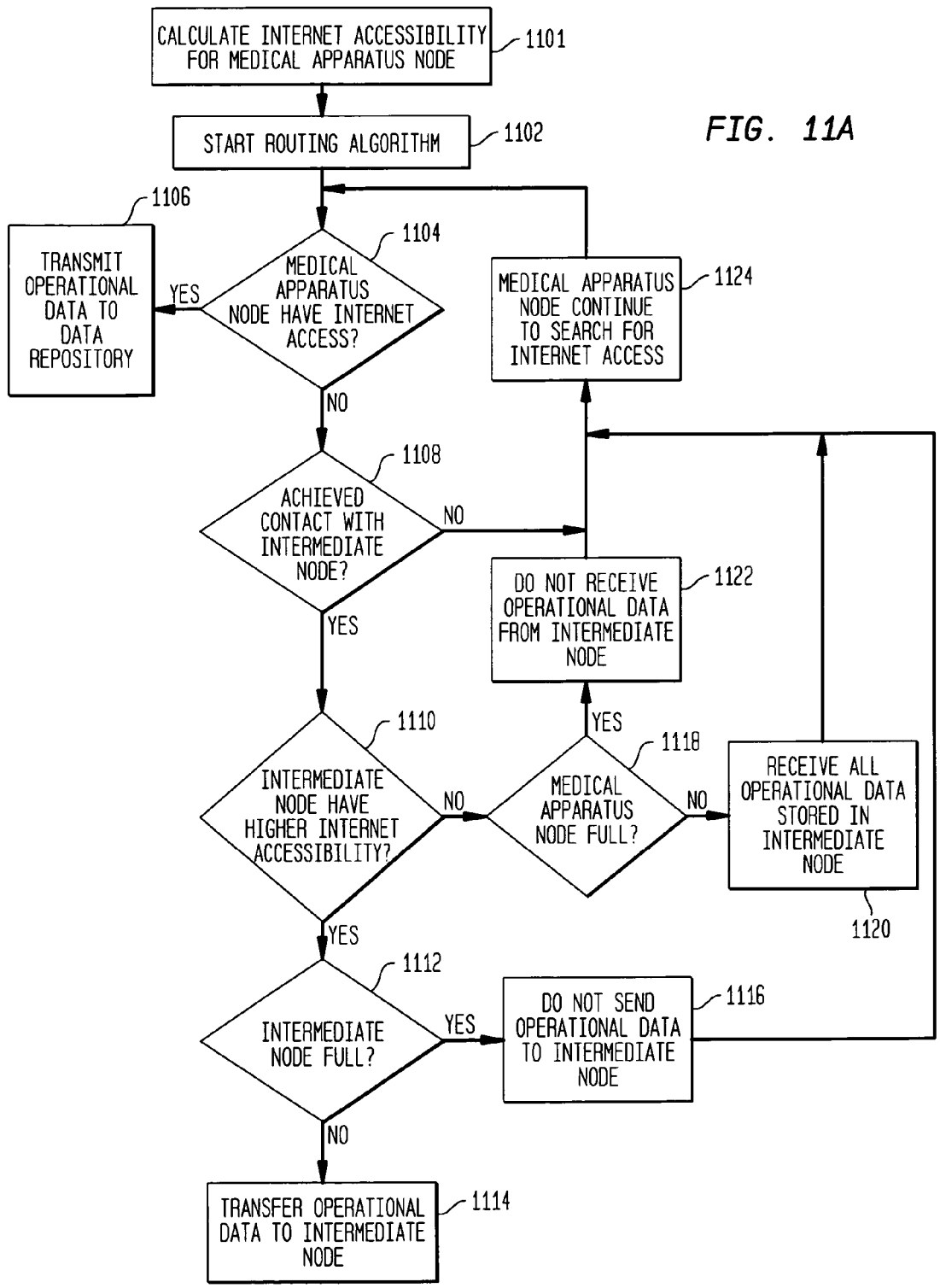
FIG. 11A is a detailed flowchart illustrating the operations performed in accordance with a routing algorithm implemented in a medical apparatus node to route operational data to the central medical location, in accordance with embodiments of the present invention.

FIG. 11A is a detailed flowchart illustrating one embodiment of a routing algorithm implemented in a data routing module 450 to select a route for captured operational data 422 to central medical location 422 over a network such as Internet 201, referred to herein as routing algorithm 1100. As shown, the routing algorithm 1100 is initiated at block 1102. At block 1104, a determination is made of the availability of direct internet access between medical apparatus node 210 and data repository 242. If direct internet access is available, captured operational data 422 is transmitted to data repository 242 via the direct internet connection at block 1106.

If a direct internet connection is not available at block 1104, algorithm 1100 determines at block 1108 whether medical apparatus node 210 has communicated with an intermediate node 220. If medical apparatus node 210 has not met an intermediate node 220, medical apparatus node 210 continues to search for a connection at block 1124. In these embodiments, medical apparatus node 210 repeats the above steps of searching for a direct internet connection or an intermediate node connection until all captured operational data 422 is transferred from medical apparatus node 210.

If at block 1108 a determination is made that a connection to an intermediate node 220 is available, calculation of the internet accessibility of medical apparatus node 210 is made at block 1101. At block 1110 a comparison of the internet accessibility 892 of medical apparatus node 210 and the internet accessibility 893 of intermediate node 220 is made. If the internet accessibility 893 of intermediate node 220 is higher than the internet accessibility 892 of medical apparatus node 210, then process 1100 advances to block 1112. At block 1112 a determination of whether intermediate node 220 has sufficient memory capacity to receive captured operational data 422 from medical apparatus node 210. If intermediate node 220 has sufficient memory to receive captured operational data 422, captured operational data 422 is transmitted from medical apparatus node 210 to intermediate node 220 at block 1114. The transmission continues until all captured operational data 422 stored in medical apparatus node 210 is transmitted, or until intermediate node 220 is full.

If at block 1112 a determination is made that intermediate node 220 does not have sufficient memory to receive captured operational data 422, at block 116 medical apparatus node 210 does not send captured operational data 422 to intermediate node 220. Medical apparatus node then continues to search for a direct internet connection or a connection to an intermediate node until all captured operational data 422 is transmitted from medical apparatus node 210.

Returning to block 1110, if at block 1110 a determination is made that the internet accessibility 893 of intermediate node 220 is lower than the internet accessibility 892 of medical apparatus node 210, the algorithm advances to block 1118. At block 1118 a determination is made if medical apparatus node 210 has sufficient memory to receive any operational data stored on intermediate node 220. If medical apparatus node 210 has sufficient memory, medical apparatus node 210 receives operational data stored on intermediate node 220 at block 1120 until intermediate node 220 has transferred all its stored operational data or until data block buffer 896 of medical apparatus node 210 is full. Medical apparatus node 210 then continues to search for a direct internet connection or a connection to an intermediate node 220 until all captured operational data 422 is transmitted from medical apparatus node 210.

If at block 1118 a determination is made that medical apparatus node 210 does not have sufficient memory, medical apparatus node 210 does not receive operational data from intermediate node 220 at block 1122. Medical apparatus node 210 then continues to search for a direct internet connection or a connection to an intermediate node 220 until all captured operational data 422 is transmitted from medical apparatus node 210.

The above description has described the routing algorithm of the present invention with respect to a connection between a medical apparatus node 210 and an intermediate node 220. It should be appreciated by one of ordinary skill in the art that intermediate nodes 220 also implement the routing algorithm to determine the most efficient route for captured operational data 422 stored thereon. As such, the above description applies equally to situations where one intermediate node is in connected to another intermediate node.

Figure 11B:
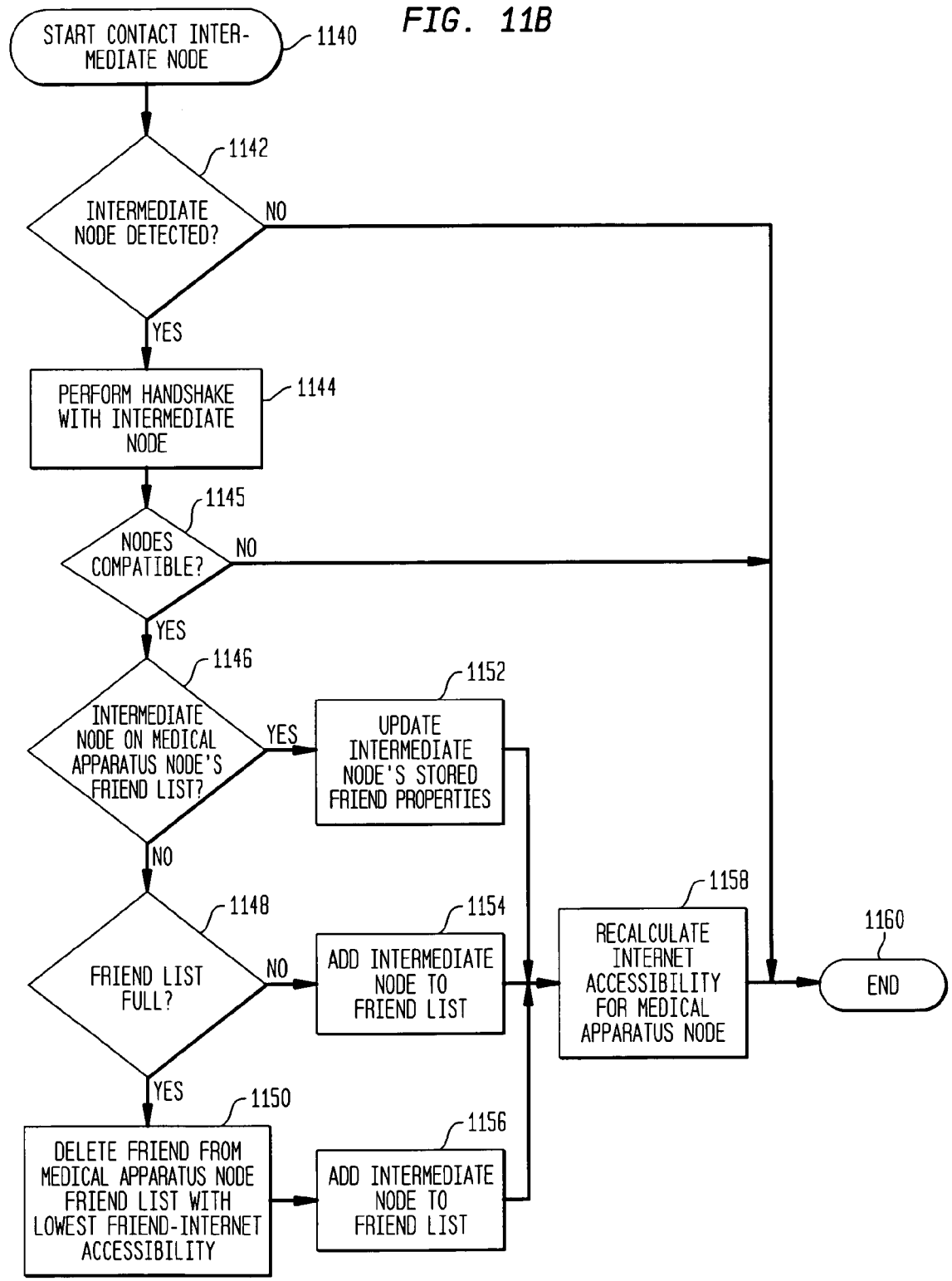
FIG. 11B is a detailed flowchart illustrating one embodiment of the process of the operations performed at a medical apparatus node achieving contact with an intermediate node of FIG. 11A.

FIG. 11B is a detailed flowchart illustrating one embodiment of the process used by medical apparatus node 210 to if determine medical apparatus node 210 has achieved contact with an intermediate node 220 at block 1108. The process is initiated at block 1140. At block 1142, a determination is made as to whether an intermediate node 220 is detected by medical apparatus node 210. If an intermediate node 220 is not detected at block 1142, the process ends at block 1160.

If at block 1142 an intermediate node 220 is detected, a handshake is performed at block 1144. At block 1145 a determination is made as to whether detected intermediate node 220 has completed a successful handshake operation with medical apparatus node 210. If a successful handshake has not been completed, the process ends at block 1160.

If a successful handshake has been completed between medical apparatus node 210 and intermediate node 220, at block 1146 a determination is made as to whether intermediate node 220 is in friend list 894 of medical apparatus node 210. If intermediate node 220 is in friend list 894 of medical apparatus node 210, friend list 894 of medical apparatus node 210 is updated at block 1152 to reflect any changes in the properties of intermediate node 220 since the last connection between the two nodes. Following the update of friend list 894 at block 1152, internet accessibility 892 of medical apparatus node 210 is recalculated at block 1158. The process then ends at block 1160.

Returning to block 1146, if intermediate node 220 is not in friend list 894 of medical apparatus node 210, at block 1148 a determination is made as to whether friend list 894 of medical apparatus node 210 is full. If friend list 894 of medical apparatus node 210 is not full, intermediate node 220 is added to friend list 894 at block 1154. After the addition of intermediate node 220 to friend list 894, internet accessibility 892 of medical apparatus node 210 is recalculated at block 1158. The process then ends at block 1160.

Returning to block 1148, if friend list 894 of medical apparatus node 210 is full, the friend of medical apparatus node 210 with the lowest friend-internet access 897 is deleted from friend list 894 at block 1150. Intermediate node 220 is then added to friend list 894 at block 1156. After the addition of intermediate node 220 to friend list 894, internet accessibility 892 of medical apparatus node 210 is recalculated at block 1158. The process then ends at block 1160.

FIG. 11C is a detailed flowchart illustrating one embodiment of the process of calculating internet accessibility 892 of medical apparatus node 210. At block 1170, a calculation of the percentage of time medical apparatus node 210 is connected to the internet is performed. At block 1172, a calculation of the friend-internet access 897 for each friend stored in friend list 894 of medical apparatus node 210 is performed. Details of the calculation of friend-internet access 897 are described below with reference to FIG. 11D. At block 1174, the process sums the friend-internet access 897 of all friends in friend list 894 of medical apparatus node 210. At block 1176 the sum calculated at block 874 is added to the percentage of time medical apparatus node 210 is connected to the internet. This sum of all friend-internet accesses 897 and percentage of time medical apparatus node 210 is connected to the internet is equal to the internet accessibility 892 of medical apparatus node 210.

Figure 11D:
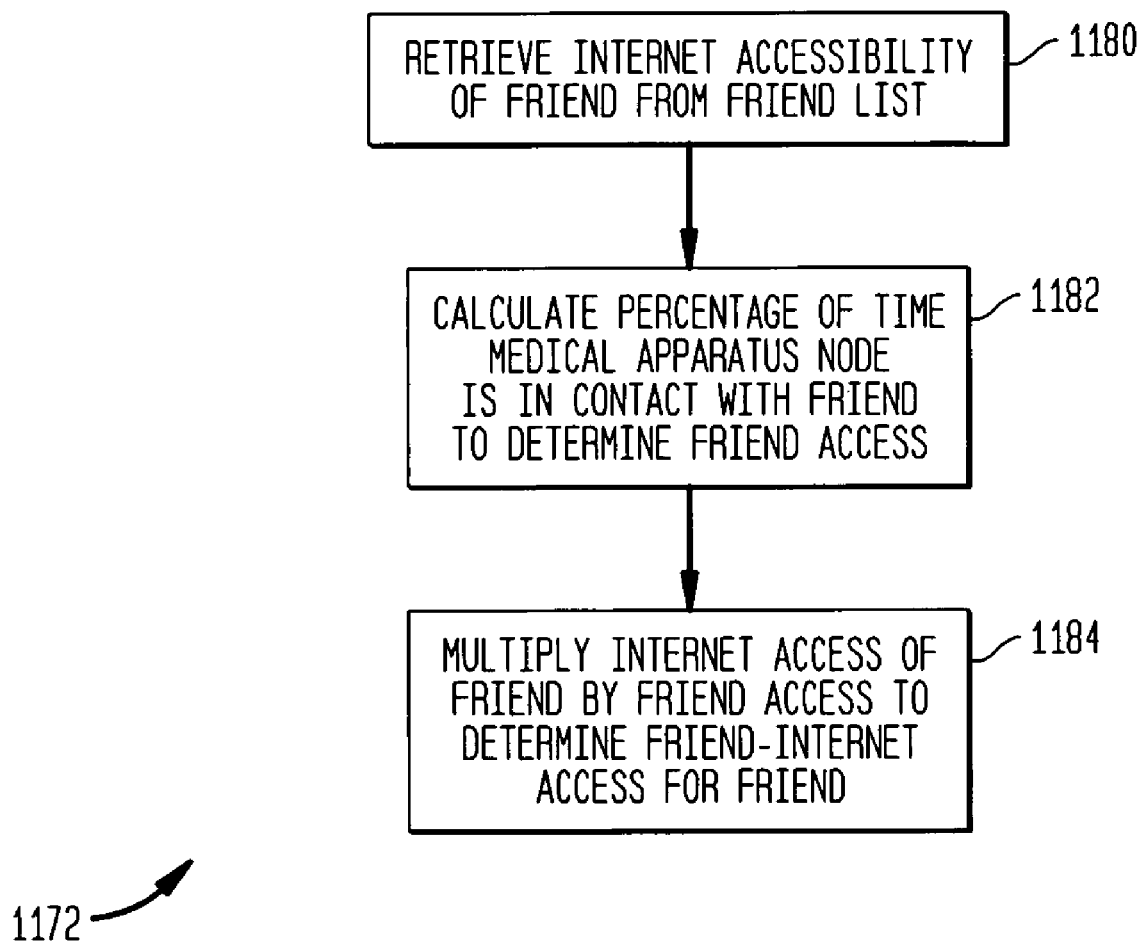
FIG. 11D is a flowchart illustrating one embodiment of the process of calculating friend-internet access of FIG. 11C.

FIG. 11D is a flowchart illustrating one embodiment of the process of calculating friend-internet access 897 of block 1172. At block 1180, internet accessibility 893 of a friend is retrieved from friend list 894. At block 1182, the percentage of time medical apparatus node is in contact with the friend is calculated. This value is shown in FIG. 8B as friend access 895. At block 1184, friend access 895 of the friend is multiplied by the internet accessibility 893 of the friend. This value calculated at block 1184 is referred to as friend-internet access 897 in FIG. 8B.

Figure 12A:
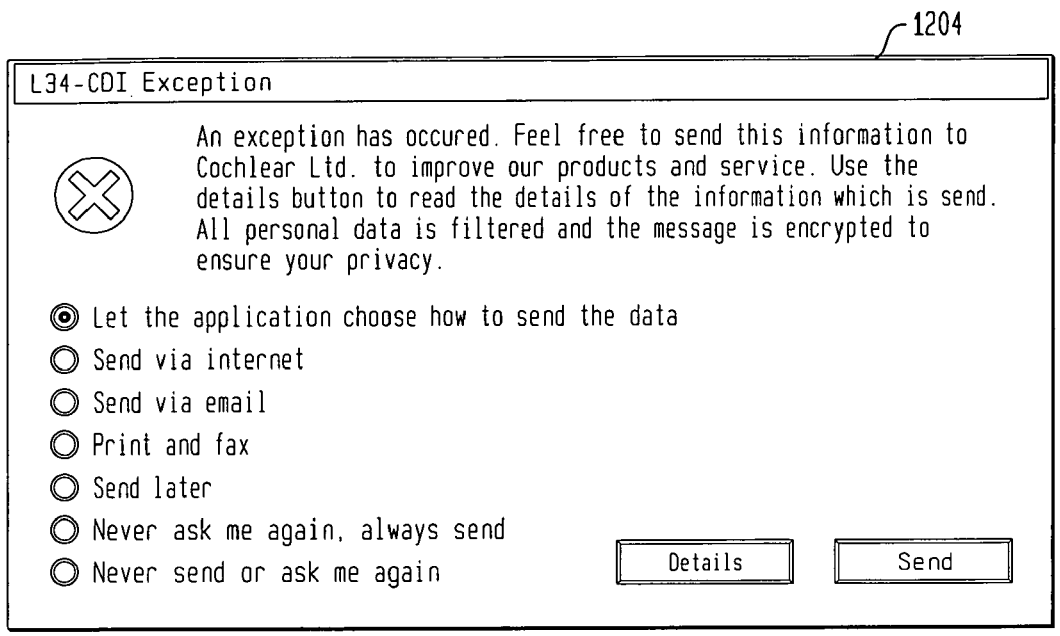
FIG. 12A is an illustration of an embodiment of a software-produced dialog box used in aspects of the present invention to notify a recipient that operational data has been captured by a medical apparatus node.
Figure 12B:
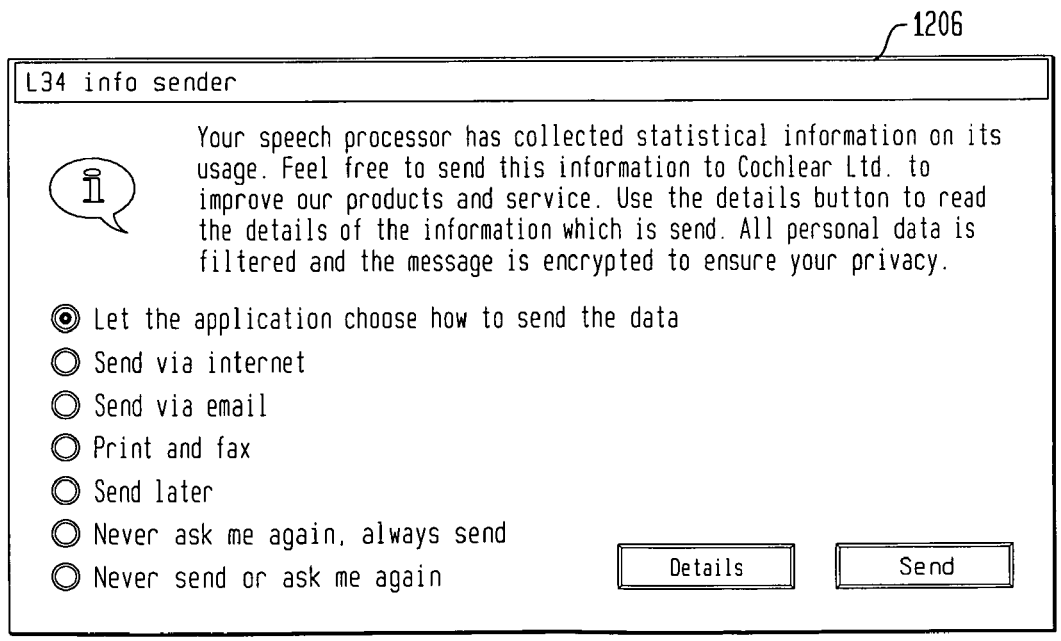
FIG. 12B is an illustration of another embodiment of a software-produced dialog box used in aspects of the present invention to notify a recipient that operational data has been captured by a medical apparatus node.

Although the present invention has been described as an automatic system for collecting operational data, the present invention should be understood to further encompass a system that uses a user interface such as a graphical user interface. In one exemplary embodiment, dialog boxes such as those shown in FIGS. 12A and 12B are displayed on the graphical user interface to notify a recipient that operational data has been captured. FIG. 12A illustrates one embodiment of a dialog box 1204 that notifies a user that an exception has occurred. FIG. 12B is an illustration of one embodiment of a dialog box 1206 that notifies a user that information on the usage of a speech processor has been captured.

In embodiments using dialog boxes to notify a user, the user may desire to be notified each time prior to transmitting captured operational data to a central medical location. In such embodiments, dialog boxes similar to dialog boxes 1204 and 1206 would notify the user of captured operational data and the user could make the decision as to whether to transmit the operational data. Similarly, as shown in FIGS. 12A and 12B, the user could be given a choice of how to send the captured operational data.

In other embodiments, a user may be notified the first time operational data is captured and could give permission for automatic transmission in the future. It should be appreciated by one of ordinary skill in the art that the user could use dialog boxes until the user becomes comfortable with automatic transmission. At this later point the user could activate automatic transmission methods described above.

In embodiments of the present invention using dialog boxes, it is envisioned that specific dialog boxes could be created to notify a user of the capture of different types of operational data. It is also envisioned that a single dialog box could be created that would be used to notify the user of the capture of a subset or of all types of captured operational data.

Due to the fact that some user may be more comfortable with technology than others, it is within the scope of the present invention to use any type of combinations of automatic transmission and dialog boxes to create a safe and comfortable transmission environment for all users of the present invention.

Further features and advantages of the present invention may be found in U.S. Provisional Patent Application No. 60/730,364 filed Oct. 27, 2005, which is hereby incorporated by reference herein.

Although the present invention has been fully described in conjunction with several embodiment thereof with reference to the accompanying drawings, it is to be understood that various changes and modifications may be apparent to those skilled in the art. For example, it should be appreciated by one of ordinary skill in the elements described above with reference to functional block diagrams may comprise more or less components than those illustrated or described, and that the functional divisions described herein are conceptual only and are provided to facilitate understanding of embodiments of the present invention. Such functional allocations, therefore, should not be construed as limiting in any way. Such changes and modifications are to be understood as included within the scope of the present invention as defined by the appended claims, unless they depart therefrom. The present embodiments are, therefore, to be considered in all respects as illustrative and not restrictive.

All documents, patents, journal articles and other materials cited in the present application are hereby incorporated by reference.

What is claimed is:

1. A method for automatically collecting at a data repository operational data from remotely distributed medical apparatus via a network that includes one or more intermediate nodes, comprising:
   automatically capturing said operational data at said medical apparatus;
   automatically selecting a route through the network for transferring said captured operational data to said data repository by:
      comparing an ability of said remotely distributed medical apparatus to transmit said operational data to said data repository to an ability of a first of the intermediate nodes to transmit said operational data to said data repository; and
      selecting the network route through the network that utilizes said first intermediate node if the ability of said first intermediate node to transmit said operational data to said data repository is superior to the ability of said remotely distributed medical apparatus to transfer said operational data to said data repository without said first intermediate node; and
   automatically transmitting said captured operational data to said data repository via said selected network route.

2. The method of claim 1, wherein said remotely distributed medical apparatus comprises:
   a portable medical device.

3. The method of claim 2, wherein said remotely distributed medical apparatus further comprises:
   at least one medical equipment associated with said portable medical device.

4. The method of claim 3, wherein said portable medical device comprises a prosthetic hearing implant, and wherein said medical equipment associated with said portable medical device comprises:
   medical equipment configured to perform at least one of implanting, maintaining, programming or servicing said prosthetic hearing implant.

5. The method of claim 2, wherein one or more of said portable medical device comprises:
   a prosthetic hearing implant.

6. The method of claim 5, wherein said prosthetic hearing implant comprises:
   a cochlear implant.

7. The method of claim 1, wherein said data repository comprises:
   a computer-based system configured to store said captured operational data.

8. The method of claim 7, wherein said computer-based system is further configured to analyze said captured operational data.

9. The method of claim 7, further comprising:
   a front-end database that temporarily stores said captured operational data and transmits said operational data to said computer-based system.

10. The method of claim 1, wherein said operational data comprises at least one of usage data or patient data.

11. The method of claim 10, wherein said usage data comprises:
   information about how a user operates and selects software or hardware components of said medical apparatus.

12. The method of claim 10, wherein said patient data includes data specific to a patient or a group of patients, comprising at least one of:
   user parameters for said remotely distributed medical apparatus, frequency of use of particular user parameters, the treatment success of particular user parameters implemented or changes in user parameters.

13. The method of claim 10, comprising:
   interrogating said remotely distributed medical apparatus to retrieve said operational data.

14. The method of claim 1, wherein said automatically capturing said operational data comprises:
   collecting said operational data from said remotely distributed medical apparatus;
   and converting said collected operational data into formatted operational data suitable for transmission over the network.

15. The method of claim 14, wherein converting said captured operational data into formatted operational data suitable for transmission over the network comprises:
converting said collected operational data into a human-readable text format.

16. The method of claim 1, wherein said automatically selecting a route through the network comprises:
automatically selecting an optimal network route for said operational data from said remotely distributed medical apparatus to said data repository based on one or more selection criteria.

17. The method of claim 16, wherein said selecting said optimal network route for said operational data comprises:
selecting a network route utilizing one or more of said intermediate nodes to route said captured operational data to said data repository, said utilized one or more of said intermediate nodes further selecting an optimal network route for said operational data from said intermediate node to said data repository based on one or more selection criteria.

18. The method of claim 1, wherein the first intermediate node is a medical apparatus of the same type as the medical apparatus from which said operational data was captured.

19. A method for automatically collecting at a data repository operational data from a remotely distributed medical apparatus via a network having one or more intermediate nodes, comprising:
automatically capturing said operational data at said medical apparatus;
automatically selecting an optimal network route through the network to transfer said captured operational data from said remotely distributed medical apparatus to said data repository based on one or more selection criteria, the optimal network route utilizing one or more of said intermediate nodes to route said captured operational data; and
automatically transmitting said captured operational data to said data repository via said selected network route;
wherein automatically selecting an optimal network route utilizing one of said intermediate nodes comprises:
contacting one of said intermediate nodes;
retrieving properties of said contacted intermediate node;
storing said retrieved properties in said remotely distributed medical apparatus, wherein said properties include the ability of said contacted intermediate node to transmit said operational data to said data repository;
calculating the ability of said remotely distributed medical apparatus to transmit said operational data to said data repository;
comparing the ability of said remotely distributed medical apparatus to transmit said operational data to said data repository to the ability of said contacted intermediate node to transmit said operational data to said data repository; and
selecting a network route utilizing said contacted intermediate node if the ability of said intermediate node to transmit said operational data to said central node location is greater than the ability of said remotely distributed medical apparatus to transfer said operational data to said data repository.

20. The method of claim 19, further comprising:
receiving any operational data stored on said contacted intermediate node to said remotely distributed medical apparatus if the ability of said intermediate node to transmit said operational data to said data repository is less than the ability of said remotely distributed medical apparatus to transfer said operational data to said data repository.

21. The method of claim 20, wherein said contacting said intermediate node comprises:
performing a handshake operation with said intermediate node; and
verifying that a successful handshake operation has been completed.

22. The method of claim 21, wherein said remotely distributed medical apparatus includes a friend list, and wherein said storing said properties retrieved from said contacted intermediate node comprises:
storing said properties in said friend list, said properties including:
the ability of said contacted intermediate node to transmit said operational data to said data repository;
the percentage of time said remotely distributed medical apparatus is connected to said contacted intermediate node; and
the mathematical product of the ability of said contacted intermediate node to transmit said operational data to said data repository and the percentage of time said remotely distributed medical apparatus is connected to said contacted intermediate node;
wherein said friend list retains said properties for a certain number of intermediate nodes that said remotely distributed medical apparatus has previously contacted.

23. The method of claim 22, wherein said calculating the ability of said remotely distributed medical apparatus to transmit said operational data to said data repository comprises:
calculating the percentage of time said remotely distributed medical apparatus is able to directly transfer said operational data to said data repository;
retrieving from said friend list for every intermediate node having properties stored in said friend list the mathematical product of the ability of a particular intermediate node to transmit said operational data to said data repository and the percentage of time said remotely distributed medical apparatus is connected to said particular intermediate node;
mathematically summing all of said calculated mathematical products; and
mathematically summing said calculated percentage of time said remotely distributed medical apparatus is able to directly transfer said operational data to said data repository and said sum of calculated mathematical products.

24. The system of claim 23, wherein said first intermediate node is a medical apparatus of the same type as the medical apparatus from which said operational data was captured.

25. The system of claim 23, wherein the medical apparatus from which said operational data is captured is a speech processor of a hearing prosthesis, and wherein said first intermediate node is a speech processor of a hearing prosthesis.

26. The method of claim 19, wherein said one or more intermediate nodes is a medical apparatus of the same type as the medical apparatus from which said operational data was captured.

27. The method of claim 19, wherein the medical apparatus from which said operational data is captured is a speech processor of a hearing prosthesis, and wherein said one or more intermediate nodes is a speech processor of a hearing prosthesis.

28. A system for automatically collecting operational data from remotely distributed medical apparatus via a network, comprising:
- a data repository;
- a remotely distributed medical apparatus configured to automatically capture said operational data; and
- at least one intermediate node connected to the network;
- wherein the system is configured to automatically select a route through the network for transferring said captured operational data from said medical apparatus to said data repository by:
  - comparing an ability of said remotely distributed medical apparatus to transmit said operational data to said data repository to an ability of a first intermediate node of said at least one intermediate node to transmit said operational data to said data repository; and
  - selecting the network route through the network that utilizes said first intermediate node if the ability of said first intermediate node to transmit said operational data to said data repository is superior to the ability of said remotely distributed medical apparatus to transfer said operational data to said data repository without said first intermediate node; and
- wherein said remotely distributed medical apparatus is configured to automatically transmit said captured operational data to said data repository via said selected network route.

29. The system of claim 28, wherein each said remotely distributed medical apparatus comprises:
- a portable medical device.

30. The system of claim 29, wherein said remotely distributed medical apparatus further comprises:
- medical equipment associated with said portable medical device.

31. The system of claim 29, wherein said portable medical device comprises a hearing prosthesis.

32. The system of claim 31, wherein said hearing prostheses comprises a cochlear implant.

33. The system of claim 31, wherein said medical equipment comprises:
- a device for performing at least one of implanting, maintaining, programming or servicing a hearing prosthesis.

34. The system of claim 28, wherein said data repository comprises:
- a computer system configured to store said captured operational data.

35. The system of claim 34, wherein said computer system is further configured to analyze said captured operational data.

36. The system of claim 34, wherein said data repository further comprises:
- a front-end database that temporarily stores said captured operational data and transmits said operational data to said computer system.

37. The system of claim 28, wherein said operational data comprises at least one of usage data or patient data.

38. The system of claim 37, wherein said usage data comprises:
- information about how a user operates and selects software or hardware components of said medical apparatus.

39. The system of claim 37, wherein said patient data includes data specific to a patient or a group of patients, the patient data comprising at least one of user parameters for said remotely distributed medical apparatus, frequency of use of particular user parameters, the treatment success of particular user parameters implemented or changes in user parameters.

40. The system of claim 28, wherein said remotely distributed medical apparatus is communicably coupled to a data transfer and acquisition module configured to capture said operational data from said medical apparatus and is configured to transmit said operation data to said data repository.

41. The system of claim 40, wherein said data transfer and acquisition module comprises:
- a data capture module configured to collect said operational data; and
- a data routing module configured to select said optimal network route for said collected operational data to said data repository, and to transmit said collected operational data via said optimal network route.

42. The system of claim 41, wherein said data capture module is further configured to convert said collected operational data into formatted operational data suitable for transmission over the network.

43. The system of claim 42, wherein said data capture module is configured to convert said collected operational data into a human-readable text format.

44. The system of claim 41, wherein said data routing module is configured to select said optimal network route based on one or more selection criteria.

45. The system of claim 25,
- wherein said selected optimal network comprises an indirect network route utilizing said first intermediate node to route said operational data to said data repository, and wherein said first intermediate node is configured to select an optimal network route for said operational data from said intermediate node to said data repository based on or more selection criteria.

46. A system for the automatic collection at a data repository of operational data from remotely distributed medical apparatus via a network, comprising:
- means for automatically capturing said operational data at said medical apparatus;
- at least one intermediate node connected to the network;
- means for automatically selecting a route through the network for transferring said captured operational data from said medical apparatus to said data repository, said means for automatically selecting a route through the network for transferring said captured operational data from said medical apparatus to said data repository including means for:
  - comparing an ability of said remotely distributed medical apparatus to transmit said operational data to said data repository to an ability of a first intermediate node of said at least one intermediate node to transmit said operational data to said data repository; and
  - selecting the network route through the network that utilizes said first intermediate node if the ability of said first intermediate node to transmit said operational data to said data repository is superior to the ability of said remotely distributed medical apparatus to transfer said operational data to said data repository without said first intermediate node; and
- means for automatically transmitting said captured operational data to said data repository location via said selected network route.

47. The system of claim 46, wherein said means for automatically capturing said operational data comprises:
- means for collecting said operational data from said remotely distributed medical apparatus; and
- means for converting said collected operational data into formatted operational data suitable for transmission over the network.

48. The system of claim 47, wherein said means for converting said captured operational data into formatted operational data suitable for transmission over the network comprises:
   means for converting said captured operational data into a human-readable text format.

49. The system of claim 46, wherein said means for automatically selecting a route through the network comprises:
   means for automatically selecting an optimal network route for said operational data from said remotely distributed medical apparatus to said data repository based on one or more selection criteria.

50. The system of claim 49, wherein said means for selecting said optimal network route for said operational data comprises:
   means for selecting a network route utilizing one or more of said intermediate nodes to route said operational data to said data repository, and wherein each utilized intermediate node includes means for further selecting an optimal network route for said operational data from said intermediate node to said data repository based on one or more selection criteria.

51. The method of claim 50, wherein the medical apparatus from which said operational data is captured is a speech processor of a hearing prosthesis, and wherein said first intermediate node is a speech processor of a hearing prosthesis.

* * * * *